US012788586B2

(12) United States Patent
Sand et al.

(10) Patent No.: US 12,788,586 B2
(45) Date of Patent: Nov. 10, 2026

(54) SACROILIAC JOINT STABILIZATION, INCLUDING IMPLANTS, SYSTEMS AND METHODS OF DELIVERING IMPLANTS

(71) Applicant: SI-Bone Inc., Santa Clara, CA (US)

(72) Inventors: Paul M. Sand, Redwood City, CA (US); Bret Schneider, San Jose, CA (US); Derek P. Lindsey, San Jose, CA (US); Francois Follini, Austin, TX (US); Nikolas F. Kerr, Milpitas, CA (US); Roxanne Simon, San Jose, CA (US); Scott A. Yerby, Montara, CA (US)

(73) Assignee: SI-Bone Inc., Santa Clara, CA (US)

( * ) Notice: Subject to any disclaimer, the term of this patent is extended or adjusted under 35 U.S.C. 154(b) by 55 days.

(21) Appl. No.: 18/951,396

(22) Filed: Nov. 18, 2024

(65) Prior Publication Data

US 2025/0161070 A1 May 22, 2025

Related U.S. Application Data

(60) Provisional application No. 63/600,475, filed on Nov. 17, 2023.

(51) Int. Cl.
*A61F 2/46* (2006.01)
*A61F 2/30* (2006.01)

(52) U.S. Cl.
CPC .. *A61F 2/4603* (2013.01); *A61F 2002/30995* (2013.01)

(58) Field of Classification Search
CPC ........ A61F 2/46; A61F 2/4601; A61F 2/4603; A61F 2/4611; A61F 2002/30995; A61F 2002/4627; A61F 2002/4681
See application file for complete search history.

(56) References Cited

U.S. PATENT DOCUMENTS

| | | | |
|---|---|---|---|
| 1,951,278 | A | 3/1934 | Ericsson |
| 2,136,471 | A | 11/1938 | Schneider |
| 2,243,717 | A | 5/1941 | Moreira |
| 2,414,882 | A | 1/1947 | Longfellow |
| 2,562,419 | A | 7/1951 | Ferris |
| 2,675,801 | A | 4/1954 | Bambara et al. |
| 2,697,433 | A | 12/1954 | Zehnder |

(Continued)

FOREIGN PATENT DOCUMENTS

| | | | |
|---|---|---|---|
| CN | 1128944 | A | 8/1996 |
| CN | 1190882 | A | 8/1998 |

(Continued)

OTHER PUBLICATIONS

Stuart et al.; U.S. Appl. No. 18/805,412 entitled "Pelvic stabilization implants, methods of use and manufacture," filed Aug. 14, 2024.

(Continued)

*Primary Examiner* — Eric S Gibson
(74) *Attorney, Agent, or Firm* — Shay Glenn LLP

(57) ABSTRACT

Methods of and instruments for positioning a sacroiliac joint implant in a dorsal trajectory down the joint. The methods may include positioning an integrated stylet and cannula adjacent the joint, removing the stylet from a cannula lumen, and advancing the implant through the cannula lumen with tamp and into the joint.

11 Claims, 22 Drawing Sheets

(56) References Cited

U.S. PATENT DOCUMENTS 3,076,453 A 2/1963 Tronzo
3,506,982 A 4/1970 Steffee
3,694,821 A 10/1972 Moritz
3,709,218 A 1/1973 Halloran
3,744,488 A 7/1973 Cox
4,059,115 A 11/1977 Jumashev et al.
4,156,943 A 6/1979 Collier
4,197,645 A 4/1980 Scheicher
4,292,964 A 10/1981 Ulrich
4,341,206 A 7/1982 Perrett et al.
4,344,190 A 8/1982 Lee et al.
4,399,813 A 8/1983 Barber
4,423,721 A 1/1984 Otte et al.
4,475,545 A 10/1984 Ender
4,501,269 A 2/1985 Bagby
4,569,338 A 2/1986 Edwards
4,612,918 A 9/1986 Slocum
4,622,959 A 11/1986 Marcus
4,630,601 A 12/1986 Harder et al.
4,638,799 A 1/1987 Moore
4,657,550 A 4/1987 Daher
4,743,256 A 5/1988 Brantigan
4,773,402 A 9/1988 Asher et al.
4,787,378 A 11/1988 Sodhi
4,790,303 A 12/1988 Steffee
4,834,757 A 5/1989 Brantigan
4,846,162 A 7/1989 Moehring
4,877,019 A 10/1989 Vives
4,878,915 A 11/1989 Brantigan
4,898,186 A 2/1990 Ikada et al.
4,904,261 A 2/1990 Dove et al.
4,950,270 A 8/1990 Bowman et al.
4,961,740 A 10/1990 Ray et al.
4,969,888 A 11/1990 Scholten et al.
4,981,481 A 1/1991 Kranz et al.
5,034,011 A 7/1991 Howland
5,034,013 A 7/1991 Kyle et al.
5,035,697 A 7/1991 Frigg
5,041,118 A 8/1991 Wasilewski
5,053,035 A 10/1991 McLaren
5,059,193 A 10/1991 Kuslich
5,066,296 A 11/1991 Chapman et al.
5,098,434 A 3/1992 Serbousek
5,102,414 A 4/1992 Kirsch
5,108,397 A 4/1992 White
5,122,141 A 6/1992 Simpson et al.
5,139,498 A 8/1992 Astudillo Ley
5,139,500 A 8/1992 Schwartz
5,147,367 A 9/1992 Ellis
5,147,402 A 9/1992 Bohler et al.
5,190,551 A 3/1993 Chin et al.
5,197,961 A 3/1993 Castle
5,242,444 A 9/1993 MacMillan
5,298,254 A 3/1994 Prewett et al.
5,334,205 A 8/1994 Cain
5,380,325 A 1/1995 Lahille et al.
5,390,683 A 2/1995 Pisharodi
5,433,718 A 7/1995 Brinker
5,443,466 A 8/1995 Shah
5,458,638 A 10/1995 Kuslich et al.
5,470,334 A 11/1995 Ross et al.
5,480,402 A 1/1996 Kim
5,569,249 A 10/1996 James et al.
5,591,235 A 1/1997 Kuslich
5,593,409 A 1/1997 Michelson
5,607,424 A 3/1997 Tropiano
5,609,635 A 3/1997 Michelson
5,609,636 A 3/1997 Kohrs et al.
5,626,616 A 5/1997 Speece
5,643,264 A 7/1997 Sherman et al.
5,645,599 A 7/1997 Samani
5,656,337 A 8/1997 Kohrs et al.
5,667,510 A 9/1997 Combs
5,669,909 A 9/1997 Zdeblick et al.
5,672,178 A 9/1997 Petersen
5,683,391 A 11/1997 Boyd
5,709,683 A 1/1998 Bagby
5,713,904 A 2/1998 Errico et al.
5,716,358 A 2/1998 Ochoa et al.
5,725,581 A 3/1998 Brånemark
5,743,912 A 4/1998 LaHille et al.
5,759,035 A 6/1998 Ricci
5,766,174 A 6/1998 Perry
5,766,252 A 6/1998 Henry et al.
5,766,261 A 6/1998 Neal et al.
5,788,699 A 8/1998 Bobst et al.
5,800,440 A 9/1998 Stead
5,868,749 A 2/1999 Reed
5,897,556 A 4/1999 Drewry et al.
5,899,906 A 5/1999 Schenk
5,928,239 A 7/1999 Mirza
5,941,885 A 8/1999 Jackson
5,961,522 A 10/1999 Mehdizadeh
5,961,554 A 10/1999 Janson et al.
6,010,507 A 1/2000 Rudloff
6,015,409 A 1/2000 Jackson
6,030,162 A 2/2000 Huebner et al.
6,053,916 A 4/2000 Moore
6,056,749 A 5/2000 Kuslich
6,066,175 A 5/2000 Henderson et al.
6,086,589 A 7/2000 Kuslich et al.
6,096,080 A 8/2000 Nicholson et al.
6,120,292 A 9/2000 Buser et al.
6,120,504 A 9/2000 Brumback et al.
6,129,730 A 10/2000 Bono et al.
6,143,031 A 11/2000 Knothe et al.
6,197,062 B1 3/2001 Fenlin
6,206,924 B1 3/2001 Timm
6,210,442 B1 4/2001 Wing et al.
6,214,049 B1 4/2001 Gayer et al.
6,221,074 B1 4/2001 Cole et al.
6,224,607 B1 5/2001 Michelson
6,241,732 B1 6/2001 Overaker et al.
6,264,657 B1 7/2001 Urbahns et al.
6,270,528 B1 8/2001 McKay
6,287,343 B1 9/2001 Kuslich et al.
6,302,885 B1 10/2001 Essiger
6,302,914 B1 10/2001 Michelson
6,306,140 B1 10/2001 Siddiqui
6,319,253 B1 11/2001 Ackeret et al.
6,406,498 B1 6/2002 Tormala et al.
6,409,768 B1 6/2002 Tepic et al.
6,436,139 B1 8/2002 Shapiro et al.
6,451,020 B1 9/2002 Zucherman et al.
6,471,707 B1 10/2002 Miller et al.
6,485,518 B1 11/2002 Cornwall et al.
6,497,707 B1 12/2002 Bowman et al.
6,517,541 B1 2/2003 Sesic
6,520,969 B2 2/2003 Lambrecht et al.
6,524,314 B1 2/2003 Dean et al.
6,527,775 B1 3/2003 Warburton
6,551,343 B1 4/2003 Törmälii et al.
6,556,857 B1 4/2003 Estes et al.
6,558,386 B1 5/2003 Cragg
6,565,566 B1 5/2003 Wagner et al.
6,575,899 B1 6/2003 Foley et al.
6,575,991 B1 6/2003 Chesbrough et al.
6,579,293 B1 6/2003 Chandran
6,582,431 B1 6/2003 Ray
6,582,467 B1 6/2003 Teitelbaum et al.
6,595,998 B2 7/2003 Johnson et al.
6,602,293 B1 8/2003 Biermann et al.
6,605,090 B1 8/2003 Trieu et al.
6,607,530 B1 8/2003 Carl et al.
6,620,163 B1 9/2003 Michelson
6,635,059 B2 10/2003 Randall et al.
6,666,868 B2 12/2003 Fallin
6,669,529 B1 12/2003 Scaries
6,673,075 B2 1/2004 Santilli
6,692,501 B2 2/2004 Michelson
6,712,852 B1 3/2004 Chung et al.
6,723,099 B1 4/2004 Goshert
6,723,100 B2 4/2004 Biedermann et al.
6,740,118 B2 5/2004 Eisermann et al.

(56) References Cited

U.S. PATENT DOCUMENTS 6,743,257 B2 6/2004 Castro
D493,533 S 7/2004 Blain
6,793,656 B1 9/2004 Mathews
6,827,740 B1 12/2004 Michelson
6,984,235 B2 1/2006 Huebner
6,989,033 B1 1/2006 Schmidt
6,991,461 B2 1/2006 Gittleman
6,993,406 B1 1/2006 Cesarano et al.
7,018,416 B2 3/2006 Hanson et al.
7,118,579 B2 10/2006 Michelson
7,147,666 B1 12/2006 Grisoni
7,175,663 B1 2/2007 Stone
7,211,085 B2 5/2007 Michelson
7,223,269 B2 5/2007 Chappuis
7,300,439 B2 11/2007 May
7,314,488 B2 1/2008 Reiley
7,335,205 B2 2/2008 Aeschlimann et al.
7,338,500 B2 3/2008 Chappuis
7,396,365 B2 7/2008 Michelson
7,452,359 B1 11/2008 Michelson
7,452,369 B2 11/2008 Barry
7,481,831 B2 1/2009 Bonutti
7,527,649 B1 5/2009 Blain
7,534,254 B1 5/2009 Michelson
7,537,616 B1 5/2009 Branch et al.
7,569,054 B2 8/2009 Michelson
7,569,059 B2 8/2009 Cerundolo
7,601,155 B2 10/2009 Petersen
7,608,097 B2 10/2009 Kyle
7,608,098 B1 10/2009 Stone et al.
7,648,509 B2 1/2010 Stark
7,686,805 B2 3/2010 Michelson
7,699,852 B2 4/2010 Frankel et al.
7,708,761 B2 5/2010 Petersen
7,727,235 B2 6/2010 Contiliano et al.
7,758,646 B2 7/2010 Khandkar et al.
7,780,704 B2 8/2010 Markworth et al.
7,846,162 B2 12/2010 Nelson et al.
7,850,732 B2 12/2010 Heinz
7,857,832 B2 12/2010 Culbert et al.
7,887,565 B2 2/2011 Michelson
7,892,265 B2 2/2011 Perez-Cruet et al.
7,901,439 B2 3/2011 Horton
7,909,832 B2 3/2011 Michelson
7,922,765 B2 4/2011 Reiley
7,942,879 B2 5/2011 Christie et al.
7,951,176 B2 5/2011 Grady et al.
8,052,728 B2 11/2011 Hestad
8,062,365 B2 11/2011 Schwab
8,066,705 B2 11/2011 Michelson
8,066,709 B2 11/2011 Michelson
8,092,505 B2 1/2012 Sommers
8,142,481 B2 3/2012 Warnick
8,202,305 B2 6/2012 Reiley
8,221,499 B2 7/2012 Lazzara et al.
8,257,398 B2 9/2012 Jackson
8,268,099 B2 9/2012 O'Neill et al.
8,308,779 B2 11/2012 Reiley
8,308,783 B2 11/2012 Morris et al.
8,317,862 B2 11/2012 Troger et al.
8,348,950 B2 1/2013 Assell et al.
8,350,186 B2 1/2013 Jones et al.
8,353,932 B2 1/2013 Jackson
8,388,667 B2 3/2013 Reiley et al.
8,394,129 B2 3/2013 Morgenstern Lopez
8,398,635 B2 3/2013 Vaidya
8,398,682 B2 3/2013 Jackson et al.
8,414,648 B2 4/2013 Reiley
8,425,570 B2 4/2013 Reiley
8,430,930 B2 4/2013 Hunt
8,440,623 B2 5/2013 Bentley et al.
8,444,693 B2 5/2013 Reiley
8,449,585 B2 5/2013 Wallenstein et al.
8,467,851 B2 6/2013 Mire et al.
8,470,004 B2 * 6/2013 Reiley ................ A61B 17/1671
606/279
8,475,505 B2 7/2013 Nebosky et al.
8,529,608 B2 9/2013 Terrill et al.
8,597,299 B2 12/2013 Farr et al.
8,608,802 B2 12/2013 Bagga et al.
D697,209 S 1/2014 Walthall et al.
8,641,737 B2 2/2014 Matthis et al.
8,641,766 B2 2/2014 Donner et al.
8,663,298 B2 3/2014 Keyer et al.
8,663,332 B1 3/2014 To et al.
8,672,986 B2 3/2014 Klaue et al.
8,734,462 B2 5/2014 Reiley et al.
8,778,026 B2 7/2014 Mauldin
8,840,651 B2 9/2014 Reiley
8,845,693 B2 9/2014 Smith et al.
8,858,601 B2 10/2014 Reiley
8,888,827 B2 11/2014 Harper et al.
8,894,685 B2 11/2014 Mickiewicz et al.
8,920,477 B2 12/2014 Reiley
8,926,670 B2 1/2015 Jackson
8,936,623 B2 1/2015 Jackson
8,945,190 B2 2/2015 Culbert et al.
8,945,193 B2 2/2015 Kirschman
8,951,254 B2 2/2015 Mayer et al.
8,951,293 B2 2/2015 Glazer et al.
8,951,295 B2 2/2015 Matityahu et al.
8,961,571 B2 2/2015 Lee et al.
8,979,911 B2 3/2015 Martineau et al.
8,986,348 B2 3/2015 Reiley
RE45,484 E 4/2015 Foley et al.
9,039,743 B2 5/2015 Reiley
9,044,321 B2 6/2015 Mauldin et al.
9,060,876 B1 6/2015 To et al.
9,089,371 B1 7/2015 Faulhaber
D738,498 S 9/2015 Frey et al.
9,131,955 B2 9/2015 Swofford
9,149,286 B1 10/2015 Greenhalgh et al.
9,173,692 B1 11/2015 Kaloostian
9,198,676 B2 12/2015 Pilgeram et al.
9,220,535 B2 12/2015 Röbling et al.
9,241,798 B2 * 1/2016 Petersen .............. A61B 17/025
9,314,286 B2 4/2016 Bottlang et al.
9,314,348 B2 4/2016 Emstad
9,358,047 B2 6/2016 Mishra et al.
9,358,057 B1 6/2016 Whipple et al.
9,375,243 B1 6/2016 Vestgaarden
9,375,323 B2 6/2016 Reiley
9,445,852 B2 9/2016 Sweeney
9,451,999 B2 9/2016 Simpson et al.
9,452,065 B1 9/2016 Lawson
9,486,264 B2 11/2016 Reiley et al.
9,498,264 B2 11/2016 Harshman et al.
9,510,872 B2 12/2016 Donner et al.
9,517,095 B2 12/2016 Vaidya
9,526,548 B2 12/2016 Asfora
9,554,909 B2 1/2017 Donner
9,561,063 B2 2/2017 Reiley
9,566,100 B2 2/2017 Asfora
9,603,613 B2 3/2017 Schoenefeld et al.
9,603,644 B2 3/2017 Sweeney
D783,821 S 4/2017 Folsom et al.
9,622,783 B2 4/2017 Reiley et al.
9,655,656 B2 5/2017 Whipple
9,662,124 B2 5/2017 Assell et al.
9,662,128 B2 5/2017 Reiley
9,662,157 B2 5/2017 Schneider et al.
9,662,158 B2 5/2017 Reiley
9,675,394 B2 6/2017 Reiley
9,743,969 B2 8/2017 Reiley
9,757,154 B2 9/2017 Donner et al.
9,763,695 B2 9/2017 Mirda
9,763,802 B2 9/2017 Baynham
9,775,648 B2 10/2017 Greenberg et al.
9,788,866 B2 10/2017 Jackson
9,808,292 B2 11/2017 Jackson
9,808,298 B2 11/2017 Stroncek et al.
9,808,299 B2 11/2017 Goel et al.
9,808,337 B2 11/2017 Housman et al.

(56) References Cited

U.S. PATENT DOCUMENTS

| | | | |
|---|---|---|---|
| 9,820,789 B2 | 11/2017 | Reiley | |
| 9,826,986 B2 | 11/2017 | Donner et al. | |
| 9,833,321 B2 | 12/2017 | Rindal et al. | |
| 9,839,448 B2 * | 12/2017 | Reckling | A61B 17/17 |
| 9,848,889 B2 | 12/2017 | Taylor et al. | |
| 9,848,892 B2 | 12/2017 | Biedermann et al. | |
| 9,883,874 B1 | 2/2018 | Vestgaarden | |
| 9,888,911 B2 | 2/2018 | Siegal | |
| 9,936,983 B2 * | 4/2018 | Mesiwala | A61B 17/846 |
| 9,949,776 B2 | 4/2018 | Mobasser et al. | |
| 9,949,843 B2 * | 4/2018 | Reiley | A61B 17/1615 |
| D816,843 S | 5/2018 | Lewis | |
| 9,956,013 B2 | 5/2018 | Reiley et al. | |
| 9,993,276 B2 | 6/2018 | Russell | |
| 9,993,277 B2 | 6/2018 | Krinke et al. | |
| 9,999,449 B2 | 6/2018 | Bonutti | |
| 10,004,547 B2 | 6/2018 | Reiley | |
| 10,034,676 B2 | 7/2018 | Donner | |
| 10,058,430 B2 | 8/2018 | Donner et al. | |
| 10,064,670 B2 | 9/2018 | Mootien et al. | |
| D831,828 S | 10/2018 | Horton et al. | |
| 10,166,022 B2 | 1/2019 | Early et al. | |
| 10,166,033 B2 | 1/2019 | Reiley et al. | |
| 10,179,014 B1 | 1/2019 | Menmuir et al. | |
| 10,188,403 B2 | 1/2019 | Mirochinik et al. | |
| 10,188,432 B2 | 1/2019 | Jackson et al. | |
| 10,188,442 B2 | 1/2019 | Mazel | |
| 10,194,951 B2 | 2/2019 | Jackson et al. | |
| 10,194,962 B2 | 2/2019 | Schneider et al. | |
| 10,201,427 B2 | 2/2019 | Mauldin et al. | |
| 10,219,841 B1 | 3/2019 | Compton et al. | |
| 10,219,885 B2 | 3/2019 | Mamo et al. | |
| D846,977 S | 4/2019 | Williams et al. | |
| D847,336 S | 4/2019 | Asfora et al. | |
| 10,245,044 B2 | 4/2019 | Petersen | |
| 10,245,076 B2 | 4/2019 | Fitzpatrick | |
| 10,245,087 B2 | 4/2019 | Donner et al. | |
| 10,258,380 B2 | 4/2019 | Sinha | |
| 10,258,393 B2 | 4/2019 | Caploon et al. | |
| 10,258,394 B2 | 4/2019 | Harshman et al. | |
| 10,271,882 B2 | 4/2019 | Biedermann et al. | |
| D847,994 S | 5/2019 | Asfora et al. | |
| 10,278,737 B2 | 5/2019 | Smith | |
| 10,285,745 B2 | 5/2019 | Cummins et al. | |
| 10,292,778 B2 | 5/2019 | Kostrzewski et al. | |
| D850,616 S | 6/2019 | Asfora et al. | |
| 10,314,631 B2 | 6/2019 | Gonzalez Blohm et al. | |
| 10,321,937 B2 | 6/2019 | Cormier et al. | |
| 10,321,945 B2 | 6/2019 | Schifano et al. | |
| 10,335,200 B2 | 7/2019 | Jackson | |
| 10,335,202 B2 | 7/2019 | Ziolo et al. | |
| 10,335,204 B2 | 7/2019 | Matthis et al. | |
| 10,335,206 B2 | 7/2019 | Nichols et al. | |
| 10,335,211 B2 | 7/2019 | Chan et al. | |
| 10,335,212 B2 | 7/2019 | Paolino et al. | |
| 10,335,216 B2 | 7/2019 | Mari et al. | |
| 10,335,217 B2 | 7/2019 | Lindner | |
| 10,342,586 B2 | 7/2019 | Schneider | |
| 10,349,983 B2 | 7/2019 | Purcell et al. | |
| 10,349,986 B2 | 7/2019 | Wall et al. | |
| 10,357,287 B2 | 7/2019 | Schlaepfer et al. | |
| 10,363,070 B2 | 7/2019 | Jackson et al. | |
| 10,363,073 B2 | 7/2019 | Raina et al. | |
| 10,363,140 B2 | 7/2019 | Mauldin et al. | |
| 10,363,143 B2 | 7/2019 | Neubardt | |
| 10,368,919 B2 | 8/2019 | Pham et al. | |
| 10,413,332 B2 | 9/2019 | Schumacher et al. | |
| 10,426,533 B2 | 10/2019 | Mauldin et al. | |
| 10,426,539 B2 | 10/2019 | Schifano et al. | |
| 10,433,880 B2 | 10/2019 | Donner et al. | |
| 10,441,319 B2 | 10/2019 | Jackson et al. | |
| 10,456,268 B2 | 10/2019 | Mercier et al. | |
| 10,463,402 B2 | 11/2019 | Biester et al. | |
| 10,478,227 B2 | 11/2019 | Leff et al. | |
| 10,485,596 B2 | 11/2019 | Koller et al. | |
| 10,492,841 B2 | 12/2019 | Hartdegen et al. | |
| 10,492,921 B2 | 12/2019 | Mcshane, III et al. | |
| 10,517,734 B2 | 12/2019 | Donner | |
| 10,531,898 B2 | 1/2020 | Boulot | |
| 10,531,904 B2 | 1/2020 | Kolb | |
| 10,537,340 B2 | 1/2020 | Mirochinik et al. | |
| D875,931 S | 2/2020 | Asfora et al. | |
| 10,555,758 B2 | 2/2020 | Magee et al. | |
| 10,588,676 B2 | 3/2020 | Kang et al. | |
| 10,588,677 B2 | 3/2020 | McDonnell | |
| 10,595,917 B2 | 3/2020 | Loftus | |
| 10,596,003 B2 | 3/2020 | Donner et al. | |
| 10,603,054 B2 | 3/2020 | Asfora et al. | |
| 10,603,055 B2 | 3/2020 | Donner et al. | |
| 10,603,087 B2 | 3/2020 | Brenzel et al. | |
| 10,603,176 B2 | 3/2020 | Arnold et al. | |
| 10,610,275 B2 | 4/2020 | Brianza | |
| 10,610,276 B2 | 4/2020 | Lutz | |
| 10,610,370 B2 | 4/2020 | Baynham | |
| 10,610,728 B2 | 4/2020 | Fano et al. | |
| 10,617,453 B2 | 4/2020 | Beckett et al. | |
| 10,631,905 B2 * | 4/2020 | Asfora | A61B 17/8625 |
| 10,653,454 B2 | 5/2020 | Frey et al. | |
| 10,653,455 B2 | 5/2020 | Lehman et al. | |
| 10,653,544 B2 | 5/2020 | Forsell | |
| 10,660,657 B2 | 5/2020 | Slobitker et al. | |
| 10,660,679 B2 | 5/2020 | Kang et al. | |
| 10,660,684 B2 | 5/2020 | Kang et al. | |
| 10,667,923 B2 | 6/2020 | Sullivan et al. | |
| 10,682,131 B2 | 6/2020 | Fallin et al. | |
| 10,682,150 B2 | 6/2020 | Stark | |
| 10,682,437 B2 | 6/2020 | Roth | |
| 10,709,570 B2 | 7/2020 | Stauffer et al. | |
| 10,711,334 B2 | 7/2020 | Patel et al. | |
| 10,729,475 B2 | 8/2020 | Childs | |
| 10,729,482 B2 | 8/2020 | Fantigrossi et al. | |
| 10,743,995 B2 | 8/2020 | Fallin et al. | |
| D895,111 S | 9/2020 | Frey et al. | |
| 10,758,274 B1 | 9/2020 | Bess et al. | |
| 10,758,283 B2 | 9/2020 | Frey et al. | |
| 10,758,285 B2 | 9/2020 | Geist et al. | |
| 10,792,053 B2 * | 10/2020 | Asfora | A61B 17/1662 |
| 10,792,074 B2 | 10/2020 | Jackson | |
| 10,799,277 B2 | 10/2020 | Kulper et al. | |
| 10,799,367 B2 | 10/2020 | Vrionis et al. | |
| 10,806,597 B2 | 10/2020 | Sournac et al. | |
| 10,842,511 B2 | 11/2020 | Patel et al. | |
| 10,842,634 B2 | 11/2020 | Pasini et al. | |
| D904,615 S | 12/2020 | Asfora et al. | |
| D905,232 S | 12/2020 | Schifano et al. | |
| 10,856,922 B2 | 12/2020 | Loke et al. | |
| 10,864,029 B2 | 12/2020 | Redmond et al. | |
| 10,898,333 B2 | 1/2021 | Cordaro | |
| 10,905,472 B2 | 2/2021 | Mari et al. | |
| 10,912,654 B2 | 2/2021 | Scheland | |
| 10,932,838 B2 | 3/2021 | Mehl et al. | |
| 10,939,944 B2 | 3/2021 | Wapner et al. | |
| 10,940,008 B2 | 3/2021 | Patel | |
| 10,959,758 B2 | 3/2021 | Mesiwala et al. | |
| 10,959,830 B2 | 3/2021 | Williams et al. | |
| 10,987,142 B2 | 4/2021 | Poelstra et al. | |
| 10,993,754 B2 | 5/2021 | Kuntz et al. | |
| 10,993,757 B2 | 5/2021 | Schifano et al. | |
| 11,000,325 B2 | 5/2021 | Sommers et al. | |
| 11,006,985 B2 | 5/2021 | Caploon et al. | |
| D921,898 S | 6/2021 | Schifano et al. | |
| D922,568 S | 6/2021 | Schifano et al. | |
| 11,020,129 B2 | 6/2021 | LaNeve et al. | |
| 11,033,309 B2 | 6/2021 | Zadeh | |
| 11,051,856 B2 | 7/2021 | Jackson | |
| 11,052,229 B2 | 7/2021 | Althoff et al. | |
| 11,058,443 B2 | 7/2021 | Siccardi et al. | |
| 11,058,550 B2 | 7/2021 | LaNeve et al. | |
| 11,058,556 B2 | 7/2021 | LaNeve et al. | |
| 11,071,573 B2 | 7/2021 | Schneider et al. | |
| D927,295 S | 8/2021 | Lanois | |
| 11,116,557 B2 | 9/2021 | Zander et al. | |
| 11,147,591 B2 | 10/2021 | Jackson | |
| 11,147,597 B2 | 10/2021 | Jackson | |

(56) References Cited

U.S. PATENT DOCUMENTS 11,147,688 B2 10/2021 Reckling et al.
11,154,402 B1 10/2021 LaNeve et al.
D935,025 S 11/2021 Schifano et al.
D935,876 S 11/2021 Lanois
11,166,821 B2 11/2021 Sazy
11,172,939 B2 11/2021 Donner et al.
11,172,969 B2 11/2021 Suddaby
11,219,534 B2 1/2022 Wall
11,224,467 B2 1/2022 Peterson et al.
11,224,490 B2 1/2022 MacMillan et al.
11,234,830 B2 2/2022 Mesiwala et al.
11,259,854 B2 3/2022 Thornes et al.
11,266,767 B2 3/2022 Roth et al.
11,273,043 B1 3/2022 Abbasi
11,284,798 B2 3/2022 Donner et al.
11,284,887 B2 3/2022 Hartdegen et al.
11,291,485 B2 4/2022 Mauldin et al.
11,298,747 B2 4/2022 Klein et al.
D951,455 S 5/2022 Ginn
D952,147 S 5/2022 Schifano et al.
11,318,020 B2 5/2022 Bohl
11,331,123 B2 5/2022 Ballard et al.
11,337,821 B2 5/2022 Mauldin et al.
11,382,755 B2 7/2022 Laneve et al.
11,382,770 B2 7/2022 Neve et al.
11,389,305 B2 7/2022 LaNeve et al.
11,413,073 B2 8/2022 Castro
11,419,652 B2 8/2022 Wickham et al.
11,419,653 B2 8/2022 Castro
11,419,654 B2 8/2022 Castro
11,432,829 B2 9/2022 Castro
11,446,069 B2 9/2022 Mauldin et al.
11,452,548 B2 9/2022 Harshman et al.
11,471,286 B2 10/2022 Mauldin et al.
11,478,287 B2 10/2022 Mauldin et al.
11,510,801 B2 11/2022 Archbold
D972,137 S 12/2022 Schifano et al.
11,517,361 B2 12/2022 Major et al.
11,544,850 B1 1/2023 Vigdorchik et al.
11,553,945 B2 1/2023 Castro
11,553,948 B2 1/2023 Haller et al.
11,553,953 B1 1/2023 Robbins
11,571,245 B2 2/2023 Stuart et al.
11,580,268 B2 2/2023 Suddaby
11,583,326 B2 2/2023 Suddaby
11,607,251 B2 3/2023 Albert et al.
11,607,256 B1 3/2023 Folsom et al.
11,633,292 B2 * 4/2023 Reiley ..................... A61F 2/447
606/279
11,660,126 B1 5/2023 Abbasi et al.
11,672,570 B2 6/2023 Stuart et al.
11,672,664 B2 6/2023 Mauldin et al.
11,678,997 B2 6/2023 Mesiwala et al.
11,684,378 B2 6/2023 Reiley et al.
11,696,771 B2 7/2023 Assell et al.
11,737,884 B2 8/2023 Vestgaarden
11,752,011 B2 9/2023 Stuart et al.
11,806,197 B2 11/2023 Frey et al.
11,806,241 B1 11/2023 Hussain et al.
11,813,009 B1 * 11/2023 Loftus ................ A61B 17/8811
11,826,035 B2 11/2023 Ichilov
11,850,156 B2 12/2023 Mauldin et al.
11,877,756 B2 1/2024 Sand et al.
11,883,296 B2 1/2024 Morgenstern Lopez et al.
11,925,475 B2 3/2024 Trabish et al.
11,931,053 B2 3/2024 LaNeve et al.
11,963,881 B2 4/2024 Josse et al.
11,969,196 B2 4/2024 Josse et al.
11,980,399 B2 5/2024 Mesiwala et al.
11,980,552 B2 5/2024 Castro
11,986,397 B2 5/2024 Reiley
11,992,410 B1 5/2024 Moseley et al.
12,004,961 B2 6/2024 Reiley
12,016,589 B2 6/2024 Murphy
12,023,079 B2 7/2024 Mauldin et al.
12,035,953 B1 7/2024 Moseley et al.
12,036,131 B2 7/2024 Castro
12,036,135 B2 7/2024 Castro
12,042,402 B2 7/2024 Stuart et al.
12,053,208 B2 8/2024 Vitale et al.
12,076,251 B2 9/2024 Mesiwala et al.
12,083,026 B2 9/2024 Reckling et al.
12,121,277 B2 * 10/2024 Loftus .................... A61B 34/20
12,127,769 B2 10/2024 Casey et al.
12,161,374 B2 12/2024 Schneider et al.
12,167,877 B2 12/2024 Harshman et al.
12,167,969 B2 12/2024 Davis et al.
12,171,439 B2 12/2024 Nayet et al.
12,201,330 B2 1/2025 Stuart et al.
12,207,828 B2 * 1/2025 Asfora ................ A61F 2/30988
12,213,886 B2 2/2025 Mauldin et al.
12,220,326 B2 2/2025 Reckling et al.
12,245,795 B2 3/2025 Spangler et al.
12,245,950 B2 3/2025 Cloutier et al.
12,251,165 B2 3/2025 Mosnier et al.
12,251,320 B2 3/2025 Casey et al.
12,262,918 B2 4/2025 Yacoub et al.
12,426,952 B2 9/2025 Ignasiak
12,426,958 B2 9/2025 Vent
12,427,027 B2 9/2025 Ginn
12,433,761 B1 10/2025 Chiou et al.
12,458,412 B2 11/2025 Lewis et al.
12,465,499 B2 11/2025 Spann
12,490,992 B2 12/2025 Perler et al.
12,514,622 B2 1/2026 Larson
12,514,644 B1 1/2026 Casey et al.
12,521,252 B2 1/2026 Josse et al.
12,530,015 B2 1/2026 Roh et al.
12,537,081 B2 1/2026 Casey et al.
12,551,354 B2 2/2026 Kowalski
12,558,131 B2 2/2026 Soo
12,564,430 B2 3/2026 Castro
12,564,447 B2 3/2026 Mosnier et al.
12,569,353 B2 3/2026 Lee et al.
12,575,862 B2 3/2026 Lewis et al.
12,575,945 B2 * 3/2026 Greenhalgh ....... A61B 17/8888
12,588,982 B2 3/2026 Ou et al.
12,599,412 B2 4/2026 Glassman et al.
12,599,696 B2 4/2026 Dunkley et al.
12,605,190 B2 4/2026 Leff et al.
12,605,250 B2 4/2026 Ginn et al.
2001/0012942 A1 8/2001 Estes et al.
2001/0046518 A1 11/2001 Sawhney
2001/0047207 A1 11/2001 Michelson
2001/0049529 A1 12/2001 Cachia et al.
2002/0019637 A1 2/2002 Frey et al.
2002/0029043 A1 3/2002 Ahrens et al.
2002/0038123 A1 3/2002 Visotsky et al.
2002/0049497 A1 4/2002 Mason
2002/0077641 A1 6/2002 Michelson
2002/0082598 A1 6/2002 Teitelbaum
2002/0120275 A1 8/2002 Schmieding et al.
2002/0120335 A1 8/2002 Angelucci et al.
2002/0128652 A1 9/2002 Ferree
2002/0143334 A1 10/2002 von Hoffmann et al.
2002/0143335 A1 10/2002 von Hoffmann et al.
2002/0151903 A1 10/2002 Takei et al.
2002/0169507 A1 11/2002 Malone
2002/0183858 A1 12/2002 Contiliano et al.
2002/0198527 A1 12/2002 Mückter
2003/0018336 A1 1/2003 Vandewalle
2003/0032961 A1 2/2003 Pelo et al.
2003/0050642 A1 3/2003 Schmieding et al.
2003/0065332 A1 4/2003 TenHuisen et al.
2003/0074000 A1 4/2003 Roth et al.
2003/0078660 A1 4/2003 Clifford et al.
2003/0083668 A1 5/2003 Rogers et al.
2003/0083688 A1 5/2003 Simonson
2003/0088251 A1 5/2003 Braun et al.
2003/0097131 A1 5/2003 Schon et al.
2003/0139815 A1 7/2003 Grooms et al.
2003/0181979 A1 9/2003 Ferree
2003/0181982 A1 9/2003 Kuslich
2003/0199983 A1 10/2003 Michelson

(56) References Cited

U.S. PATENT DOCUMENTS

2003/0229358 A1 12/2003 Errico et al.
2003/0233146 A1 12/2003 Grinberg et al.
2003/0233147 A1 12/2003 Nicholson et al.
2004/0010315 A1 1/2004 Song
2004/0024458 A1 2/2004 Senegas et al.
2004/0034422 A1 2/2004 Errico et al.
2004/0073216 A1 4/2004 Lieberman
2004/0073314 A1 4/2004 White et al.
2004/0082955 A1 4/2004 Zirkle
2004/0087948 A1 5/2004 Suddaby
2004/0097927 A1 5/2004 Yeung et al.
2004/0106925 A1 6/2004 Culbert
2004/0117022 A1 6/2004 Marnay et al.
2004/0127990 A1 7/2004 Bartish, Jr. et al.
2004/0138750 A1 7/2004 Mitchell
2004/0138753 A1 7/2004 Ferree
2004/0147929 A1 7/2004 Biedermann et al.
2004/0158324 A1 8/2004 Lange
2004/0176287 A1 9/2004 Harrison et al.
2004/0176853 A1 9/2004 Sennett et al.
2004/0181282 A1 9/2004 Zucherman et al.
2004/0186572 A1 9/2004 Lange et al.
2004/0210221 A1 10/2004 Kozak et al.
2004/0210227 A1 10/2004 Trail et al.
2004/0225360 A1 11/2004 Malone
2004/0230305 A1 11/2004 Gorensek et al.
2004/0260286 A1 12/2004 Ferree
2004/0267369 A1 12/2004 Lyons et al.
2005/0015059 A1 1/2005 Sweeney
2005/0015146 A1 1/2005 Louis et al.
2005/0033435 A1 2/2005 Belliard et al.
2005/0037319 A1 2/2005 Bulard et al.
2005/0049590 A1 3/2005 Alleyne et al.
2005/0055023 A1 3/2005 Sohngen et al.
2005/0070905 A1 3/2005 Donnelly et al.
2005/0070907 A1 3/2005 Abernathie
2005/0071004 A1 3/2005 Re et al.
2005/0075641 A1 4/2005 Singhatat et al.
2005/0080415 A1 4/2005 Keyer et al.
2005/0107878 A1 5/2005 Conchy
2005/0112397 A1 5/2005 Rolfe et al.
2005/0113919 A1 5/2005 Cragg et al.
2005/0124993 A1 6/2005 Chappuis
2005/0131409 A1 6/2005 Chervitz et al.
2005/0137605 A1 6/2005 Assell et al.
2005/0143837 A1 6/2005 Ferree
2005/0149192 A1 7/2005 Zucherman et al.
2005/0158149 A1 7/2005 Panasik et al.
2005/0159749 A1 7/2005 Levy et al.
2005/0159812 A1 7/2005 Dinger et al.
2005/0165398 A1 7/2005 Reiley
2005/0192572 A1 9/2005 Abdelgany et al.
2005/0216017 A1 9/2005 Fielding
2005/0216082 A1 9/2005 Wilson et al.
2005/0228384 A1 10/2005 Zucherman et al.
2005/0228388 A1 10/2005 Brodke et al.
2005/0246021 A1 11/2005 Ringeisen et al.
2005/0251146 A1 11/2005 Martz et al.
2005/0273101 A1 12/2005 Schumacher
2005/0277940 A1 12/2005 Neff
2006/0004396 A1 1/2006 Easley et al.
2006/0025771 A1 2/2006 Jackson
2006/0036247 A1 2/2006 Michelson
2006/0036251 A1 2/2006 Reiley
2006/0036252 A1 2/2006 Baynham et al.
2006/0054171 A1 3/2006 Dall
2006/0058793 A1 3/2006 Michelson
2006/0058800 A1 3/2006 Ainsworth et al.
2006/0062825 A1 3/2006 Maccecchini
2006/0084986 A1 4/2006 Grinberg et al.
2006/0089644 A1 4/2006 Felix
2006/0089656 A1 4/2006 Allard et al.
2006/0095038 A1 5/2006 Jackson
2006/0111779 A1 5/2006 Petersen
2006/0129247 A1 6/2006 Brown et al.
2006/0142772 A1 6/2006 Ralph et al.
2006/0161163 A1 7/2006 Shino
2006/0178673 A1 8/2006 Curran
2006/0195094 A1 8/2006 McGraw et al.
2006/0217717 A1 9/2006 Whipple
2006/0235387 A1 10/2006 Peterman
2006/0241600 A1 10/2006 Ensign et al.
2006/0241776 A1 10/2006 Brown et al.
2006/0271054 A1 11/2006 Sucec et al.
2006/0293662 A1 12/2006 Boyer, II et al.
2007/0027544 A1 2/2007 McCord et al.
2007/0038219 A1 2/2007 Matthis et al.
2007/0049933 A1 3/2007 Ahn et al.
2007/0066977 A1 3/2007 Assell et al.
2007/0073295 A1 3/2007 Biederman et al.
2007/0083265 A1 4/2007 Malone
2007/0088362 A1 4/2007 Bonutti et al.
2007/0093841 A1 4/2007 Hoogland
2007/0093898 A1 4/2007 Schwab et al.
2007/0106383 A1 5/2007 Abdou
2007/0149976 A1 6/2007 Hale et al.
2007/0156144 A1 7/2007 Ulrich et al.
2007/0156241 A1 7/2007 Reiley et al.
2007/0156246 A1 7/2007 Meswania et al.
2007/0161985 A1 7/2007 Demakas et al.
2007/0161989 A1 7/2007 Heinz et al.
2007/0173820 A1 7/2007 Trieu
2007/0219634 A1 9/2007 Greenhalgh et al.
2007/0233080 A1 10/2007 Na et al.
2007/0233146 A1 10/2007 Henniges et al.
2007/0233247 A1 10/2007 Schwab
2007/0250166 A1 10/2007 McKay
2007/0270833 A1 11/2007 Bonutti et al.
2007/0270858 A1 11/2007 Trieu et al.
2007/0270879 A1 11/2007 Isaza et al.
2007/0276500 A1 11/2007 Zucherman et al.
2007/0282443 A1 12/2007 Globerman et al.
2008/0021454 A1 1/2008 Chao et al.
2008/0021455 A1 1/2008 Chao et al.
2008/0021456 A1 1/2008 Gupta et al.
2008/0021461 A1 1/2008 Barker et al.
2008/0021480 A1 1/2008 Chin et al.
2008/0065093 A1 3/2008 Assell et al.
2008/0065215 A1 3/2008 Reiley
2008/0071356 A1 3/2008 Greenhalgh et al.
2008/0109083 A1 5/2008 Van Hoeck et al.
2008/0125868 A1 5/2008 Branemark et al.
2008/0132901 A1 6/2008 Recoules-Arche et al.
2008/0140082 A1* 6/2008 Erdem ............... A61B 17/8805
606/92
2008/0147079 A1 6/2008 Chin et al.
2008/0154314 A1 6/2008 McDevitt
2008/0154374 A1 6/2008 Labrom
2008/0161810 A1 7/2008 Melkent
2008/0161927 A1 7/2008 Savage et al.
2008/0183204 A1 7/2008 Greenhalgh et al.
2008/0234758 A1 9/2008 Fisher et al.
2008/0249579 A1 10/2008 Taylor
2008/0255562 A1 10/2008 Gil et al.
2008/0255618 A1 10/2008 Fisher et al.
2008/0255622 A1 10/2008 Mickiewicz et al.
2008/0255664 A1 10/2008 Hogendijk et al.
2008/0255666 A1 10/2008 Fisher et al.
2008/0255667 A1 10/2008 Horton
2008/0275454 A1 11/2008 Geibel
2008/0294202 A1 11/2008 Peterson et al.
2008/0306554 A1 12/2008 Mckinley
2009/0012529 A1 1/2009 Blain et al.
2009/0018660 A1 1/2009 Roush
2009/0024174 A1 1/2009 Stark
2009/0036927 A1 2/2009 Vestgaarden
2009/0037148 A1 2/2009 Lin et al.
2009/0043393 A1 2/2009 Duggal et al.
2009/0082810 A1 3/2009 Bhatnagar et al.
2009/0082869 A1 3/2009 Slemker et al.
2009/0099602 A1 4/2009 Aflatoon
2009/0099610 A1 4/2009 Johnson et al.
2009/0105770 A1 4/2009 Berrevooets et al.
2009/0118771 A1 5/2009 Gonzalez-Hernandez

(56) References Cited

U.S. PATENT DOCUMENTS

| | | | | |
|---|---|---|---|---|
| 2009/0131986 | A1 | 5/2009 | Lee et al. | |
| 2009/0138053 | A1* | 5/2009 | Assell | A61F 2/4611 606/301 |
| 2009/0157119 | A1 | 6/2009 | Hale | |
| 2009/0163920 | A1 | 6/2009 | Hochschuler et al. | |
| 2009/0171394 | A1 | 7/2009 | Adbou | |
| 2009/0187247 | A1 | 7/2009 | Metcalf, Jr. et al. | |
| 2009/0216238 | A1* | 8/2009 | Stark | A61F 2/4657 606/329 |
| 2009/0270929 | A1 | 10/2009 | Suddaby | |
| 2009/0287254 | A1 | 11/2009 | Nayet et al. | |
| 2009/0312798 | A1 | 12/2009 | Varela | |
| 2009/0319043 | A1 | 12/2009 | McDevitt et al. | |
| 2009/0324678 | A1 | 12/2009 | Thorne et al. | |
| 2010/0003638 | A1 | 1/2010 | Collins et al. | |
| 2010/0022535 | A1 | 1/2010 | Lee et al. | |
| 2010/0076502 | A1 | 3/2010 | Guyer et al. | |
| 2010/0081107 | A1 | 4/2010 | Bagambisa et al. | |
| 2010/0094290 | A1 | 4/2010 | Vaidya | |
| 2010/0094295 | A1 | 4/2010 | Schnieders et al. | |
| 2010/0094420 | A1 | 4/2010 | Grohowski | |
| 2010/0106194 | A1 | 4/2010 | Bonutti et al. | |
| 2010/0106195 | A1 | 4/2010 | Serhan et al. | |
| 2010/0114174 | A1 | 5/2010 | Jones et al. | |
| 2010/0114317 | A1 | 5/2010 | Lambrecht et al. | |
| 2010/0131011 | A1 | 5/2010 | Stark | |
| 2010/0137990 | A1 | 6/2010 | Apatsidis et al. | |
| 2010/0145461 | A1 | 6/2010 | Landry et al. | |
| 2010/0160977 | A1 | 6/2010 | Gephart et al. | |
| 2010/0168798 | A1 | 7/2010 | Clineff | |
| 2010/0191292 | A1 | 7/2010 | DeMeo et al. | |
| 2010/0228301 | A1 | 9/2010 | Greenhalgh et al. | |
| 2010/0234890 | A1 | 9/2010 | Alamin et al. | |
| 2010/0262242 | A1 | 10/2010 | Chavatte et al. | |
| 2010/0268228 | A1 | 10/2010 | Petersen | |
| 2010/0280619 | A1 | 11/2010 | Yuan et al. | |
| 2010/0280622 | A1 | 11/2010 | McKinley | |
| 2010/0286778 | A1 | 11/2010 | Eisermann et al. | |
| 2010/0298889 | A1 | 11/2010 | Wilberg et al. | |
| 2010/0331851 | A1 | 12/2010 | Huene | |
| 2010/0331893 | A1 | 12/2010 | Geist et al. | |
| 2011/0009869 | A1 | 1/2011 | Marino et al. | |
| 2011/0009966 | A1 | 1/2011 | Michelson | |
| 2011/0022089 | A1 | 1/2011 | Assell et al. | |
| 2011/0029019 | A1 | 2/2011 | Ainsworth et al. | |
| 2011/0040338 | A1 | 2/2011 | Jackson | |
| 2011/0040362 | A1* | 2/2011 | Godara | A61B 18/1482 607/116 |
| 2011/0046737 | A1 | 2/2011 | Teisen | |
| 2011/0060373 | A1 | 3/2011 | Russell et al. | |
| 2011/0060375 | A1 | 3/2011 | Bonutti | |
| 2011/0066190 | A1 | 3/2011 | Schaller et al. | |
| 2011/0082551 | A1 | 4/2011 | Kraus | |
| 2011/0093020 | A1 | 4/2011 | Wu | |
| 2011/0098747 | A1 | 4/2011 | Donner et al. | |
| 2011/0098816 | A1 | 4/2011 | Jacob et al. | |
| 2011/0098817 | A1 | 4/2011 | Eckhardt et al. | |
| 2011/0106175 | A1 | 5/2011 | Rezach | |
| 2011/0153018 | A1 | 6/2011 | Walters et al. | |
| 2011/0160866 | A1 | 6/2011 | Laurence et al. | |
| 2011/0178561 | A1 | 7/2011 | Roh | |
| 2011/0184417 | A1 | 7/2011 | Kitch et al. | |
| 2011/0184518 | A1 | 7/2011 | Trieu | |
| 2011/0184519 | A1 | 7/2011 | Trieu | |
| 2011/0184520 | A1 | 7/2011 | Trieu | |
| 2011/0196372 | A1 | 8/2011 | Murase | |
| 2011/0213432 | A1 | 9/2011 | Geist et al. | |
| 2011/0230966 | A1 | 9/2011 | Trieu | |
| 2011/0238074 | A1 | 9/2011 | Ek | |
| 2011/0238124 | A1 | 9/2011 | Richelsoph | |
| 2011/0238181 | A1 | 9/2011 | Trieu | |
| 2011/0245930 | A1 | 10/2011 | Alley et al. | |
| 2011/0257755 | A1 | 10/2011 | Bellemere et al. | |
| 2011/0264229 | A1 | 10/2011 | Donner | |
| 2011/0276098 | A1 | 11/2011 | Biedermann et al. | |
| 2011/0295272 | A1 | 12/2011 | Assell et al. | |
| 2011/0295370 | A1 | 12/2011 | Suh et al. | |
| 2011/0313471 | A1 | 12/2011 | McLean et al. | |
| 2011/0313532 | A1 | 12/2011 | Hunt | |
| 2011/0319995 | A1 | 12/2011 | Voellmicke et al. | |
| 2012/0004730 | A1 | 1/2012 | Castro | |
| 2012/0035667 | A1 | 2/2012 | Van Nortwick et al. | |
| 2012/0083887 | A1 | 4/2012 | Purcell et al. | |
| 2012/0095560 | A1 | 4/2012 | Donner | |
| 2012/0165872 | A1 | 6/2012 | Alamin et al. | |
| 2012/0179256 | A1 | 7/2012 | Reiley | |
| 2012/0191191 | A1 | 7/2012 | Trieu | |
| 2012/0215315 | A1 | 8/2012 | Hochschuler et al. | |
| 2012/0226318 | A1 | 9/2012 | Wenger et al. | |
| 2012/0253398 | A1 | 10/2012 | Metcalf et al. | |
| 2012/0271424 | A1 | 10/2012 | Crawford | |
| 2012/0277866 | A1 | 11/2012 | Kalluri et al. | |
| 2012/0296428 | A1 | 11/2012 | Donner | |
| 2012/0323285 | A1 | 12/2012 | Assell et al. | |
| 2013/0018427 | A1 | 1/2013 | Pham et al. | |
| 2013/0030456 | A1 | 1/2013 | Assell et al. | |
| 2013/0030529 | A1 | 1/2013 | Hunt | |
| 2013/0035727 | A1 | 2/2013 | Datta | |
| 2013/0053852 | A1 | 2/2013 | Greenhalgh et al. | |
| 2013/0053854 | A1 | 2/2013 | Schoenefeld et al. | |
| 2013/0053902 | A1 | 2/2013 | Trudeau | |
| 2013/0053963 | A1 | 2/2013 | Davenport | |
| 2013/0072984 | A1 | 3/2013 | Robinson | |
| 2013/0085535 | A1 | 4/2013 | Greenhalgh et al. | |
| 2013/0096683 | A1 | 4/2013 | Kube | |
| 2013/0116793 | A1 | 5/2013 | Kloss | |
| 2013/0123850 | A1 | 5/2013 | Schoenefeld et al. | |
| 2013/0123935 | A1 | 5/2013 | Hunt et al. | |
| 2013/0131678 | A1 | 5/2013 | Dahners | |
| 2013/0144343 | A1 | 6/2013 | Arnett et al. | |
| 2013/0158609 | A1 | 6/2013 | Mikhail et al. | |
| 2013/0172736 | A1 | 7/2013 | Abdou | |
| 2013/0197590 | A1 | 8/2013 | Assell et al. | |
| 2013/0203088 | A1 | 8/2013 | Baerlecken et al. | |
| 2013/0218215 | A1 | 8/2013 | Ginn et al. | |
| 2013/0218282 | A1 | 8/2013 | Hunt | |
| 2013/0231746 | A1 | 9/2013 | Ginn et al. | |
| 2013/0237988 | A1 | 9/2013 | Mauldin | |
| 2013/0245703 | A1 | 9/2013 | Warren et al. | |
| 2013/0245763 | A1 | 9/2013 | Mauldin | |
| 2013/0253595 | A1 | 9/2013 | Zucherman et al. | |
| 2013/0267836 | A1 | 10/2013 | Mauldin et al. | |
| 2013/0267961 | A1 | 10/2013 | Mauldin et al. | |
| 2013/0267989 | A1 | 10/2013 | Mauldin et al. | |
| 2013/0274890 | A1 | 10/2013 | McKay | |
| 2013/0325129 | A1 | 12/2013 | Huang | |
| 2013/0338722 | A1 | 12/2013 | Yalizis | |
| 2014/0012334 | A1 | 1/2014 | Armstrong et al. | |
| 2014/0012340 | A1* | 1/2014 | Beck | A61B 17/8645 606/86 R |
| 2014/0012384 | A1 | 1/2014 | Kana et al. | |
| 2014/0031934 | A1 | 1/2014 | Trieu | |
| 2014/0031935 | A1 | 1/2014 | Donner et al. | |
| 2014/0031938 | A1 | 1/2014 | Lechmann et al. | |
| 2014/0031939 | A1 | 1/2014 | Wolfe et al. | |
| 2014/0046380 | A1 | 2/2014 | Asfora | |
| 2014/0074175 | A1 | 3/2014 | Ehler et al. | |
| 2014/0088596 | A1 | 3/2014 | Assell et al. | |
| 2014/0088707 | A1 | 3/2014 | Donner et al. | |
| 2014/0094860 | A1 | 4/2014 | Reimels | |
| 2014/0121776 | A1 | 5/2014 | Hunt | |
| 2014/0135927 | A1 | 5/2014 | Pavlov et al. | |
| 2014/0142700 | A1 | 5/2014 | Donner et al. | |
| 2014/0172026 | A1 | 6/2014 | Biedermann et al. | |
| 2014/0172027 | A1 | 6/2014 | Biedermann et al. | |
| 2014/0200618 | A1 | 7/2014 | Donner et al. | |
| 2014/0207240 | A1 | 7/2014 | Stoffman et al. | |
| 2014/0257294 | A1 | 9/2014 | Gedet et al. | |
| 2014/0257408 | A1 | 9/2014 | Trieu et al. | |
| 2014/0276846 | A1 | 9/2014 | Mauldin et al. | |
| 2014/0276851 | A1* | 9/2014 | Schneider | A61B 17/92 606/84 |
| 2014/0277139 | A1 | 9/2014 | Vrionis et al. | |
| 2014/0277165 | A1 | 9/2014 | Katzman et al. | |

(56) References Cited

U.S. PATENT DOCUMENTS

2014/0277460 A1 9/2014 Schifano et al.
2014/0277462 A1 9/2014 Yerby et al.
2014/0277463 A1 9/2014 Yerby et al.
2014/0288649 A1 9/2014 Hunt
2014/0288650 A1 9/2014 Hunt
2014/0296982 A1 10/2014 Cheng
2014/0330382 A1 11/2014 Mauldin
2014/0364917 A1 12/2014 Sandstrom et al.
2015/0012051 A1 1/2015 Warren et al.
2015/0039037 A1 2/2015 Donner et al.
2015/0080951 A1 3/2015 Yeh
2015/0080972 A1 3/2015 Chin et al.
2015/0094765 A1 4/2015 Donner et al.
2015/0112444 A1 4/2015 Aksu
2015/0147397 A1 5/2015 Altschuler
2015/0150683 A1 6/2015 Donner et al.
2015/0173805 A1 6/2015 Donner et al.
2015/0173904 A1 6/2015 Stark
2015/0182268 A1 7/2015 Donner et al.
2015/0190149 A1 7/2015 Assell et al.
2015/0190187 A1 7/2015 Parent et al.
2015/0198196 A1 7/2015 Horiuchi
2015/0209094 A1 7/2015 Anderson
2015/0216566 A1 8/2015 Mikhail et al.
2015/0238203 A1 8/2015 Asfora
2015/0250513 A1 9/2015 De Lavigne Sainte
2015/0250611 A1 9/2015 Schifano et al.
2015/0250612 A1 9/2015 Schifano et al.
2015/0257892 A1 9/2015 Lechmann et al.
2015/0313720 A1 11/2015 Lorio
2015/0320450 A1 11/2015 Mootien et al.
2015/0320451 A1 11/2015 Mootien et al.
2015/0320469 A1 11/2015 Biedermann et al.
2015/0342753 A1 12/2015 Donner et al.
2016/0000488 A1 1/2016 Hi
2016/0022429 A1 1/2016 Greenhalgh et al.
2016/0095711 A1 4/2016 Castro, III
2016/0095721 A1 4/2016 Schell et al.
2016/0100870 A1 4/2016 Lavigne et al.
2016/0106477 A1 4/2016 Hynes et al.
2016/0106479 A1 4/2016 Hynes et al.
2016/0120661 A1* 5/2016 Schell ................ A61B 17/8605 623/17.11
2016/0143671 A1 5/2016 Jimenez
2016/0157897 A1 6/2016 Vaidya
2016/0157908 A1 6/2016 Cawley et al.
2016/0166291 A1 6/2016 Goel et al.
2016/0166301 A1 6/2016 Papangelou et al.
2016/0175113 A1 6/2016 Lins
2016/0184103 A1 6/2016 Fonte et al.
2016/0213487 A1 7/2016 Wilson et al.
2016/0242820 A1 8/2016 Whipple et al.
2016/0242912 A1 8/2016 Lindsey et al.
2016/0249940 A1 9/2016 Stark
2016/0287171 A1* 10/2016 Sand .................... A61B 5/4851
2016/0287301 A1 10/2016 Mehl et al.
2016/0310188 A1 10/2016 Marino et al.
2016/0310197 A1 10/2016 Black et al.
2016/0324643 A1 11/2016 Donner et al.
2016/0324656 A1 11/2016 Morris et al.
2016/0374727 A1 12/2016 Greenhalgh et al.
2017/0014235 A1 1/2017 Jones et al.
2017/0020573 A1 1/2017 Cain et al.
2017/0020585 A1 1/2017 Harshman et al.
2017/0086885 A1 3/2017 Duncan et al.
2017/0128083 A1 5/2017 Germain
2017/0128214 A1 5/2017 Mayer
2017/0135733 A1 5/2017 Donner et al.
2017/0135737 A1 5/2017 Krause
2017/0143513 A1 5/2017 Sandstrom et al.
2017/0156879 A1 6/2017 Janowski
2017/0156880 A1 6/2017 Halverson et al.
2017/0202511 A1 7/2017 Chang et al.
2017/0209155 A1 7/2017 Petersen
2017/0216036 A1 8/2017 Cordaro
2017/0224393 A1 8/2017 Lavigne et al.
2017/0246000 A1 8/2017 Pavlov et al.
2017/0258498 A1 9/2017 Redmond et al.
2017/0258506 A1 9/2017 Redmond et al.
2017/0258606 A1 9/2017 Afzal
2017/0266007 A1 9/2017 Gelaude et al.
2017/0296344 A1 10/2017 Souza et al.
2017/0303938 A1 10/2017 Rindal et al.
2017/0333205 A1 11/2017 Joly et al.
2017/0348034 A1 12/2017 LaPierre et al.
2017/0354442 A1 12/2017 Kim et al.
2017/0360570 A1 12/2017 Berndt et al.
2018/0008256 A1 1/2018 Fallin et al.
2018/0036041 A1 2/2018 Pham et al.
2018/0042735 A1 2/2018 Schell et al.
2018/0092677 A1 4/2018 Peterson et al.
2018/0104063 A1 4/2018 Asaad
2018/0104068 A1 4/2018 Sack
2018/0110624 A1 4/2018 Arnone
2018/0110626 A1 4/2018 McShane, III et al.
2018/0200063 A1 7/2018 Kahmer et al.
2018/0214192 A1 8/2018 Roby et al.
2018/0228613 A1 8/2018 Jones et al.
2018/0228617 A1 8/2018 Srour et al.
2018/0228621 A1 8/2018 Reiley et al.
2018/0235643 A1 8/2018 Lins et al.
2018/0243097 A1 8/2018 Jones et al.
2018/0256232 A1 9/2018 Russell
2018/0256351 A1 9/2018 Bishop et al.
2018/0256352 A1 9/2018 Nyahay et al.
2018/0256361 A1 9/2018 Bishop et al.
2018/0280139 A1 10/2018 Jones et al.
2018/0280140 A1 10/2018 Jones et al.
2018/0289504 A1 10/2018 Arthurs et al.
2018/0296227 A1 10/2018 Meek et al.
2018/0296347 A1 10/2018 Hamzey et al.
2018/0296363 A1 10/2018 Berry
2018/0303520 A1 10/2018 Rajpal
2018/0303623 A1 10/2018 Shoshtaev
2018/0303624 A1 10/2018 Shoshtaev
2018/0317971 A1 11/2018 Prevost
2018/0360512 A1 12/2018 Mari
2018/0368894 A1 12/2018 Wieland et al.
2019/0000636 A1 1/2019 Kim et al.
2019/0008562 A1 1/2019 Melton et al.
2019/0046684 A1 2/2019 Roth
2019/0076258 A1 3/2019 Black et al.
2019/0076266 A1 3/2019 Trudeau et al.
2019/0083270 A1 3/2019 Milz et al.
2019/0091027 A1 3/2019 Asaad et al.
2019/0117827 A1 4/2019 Roth
2019/0125371 A1 5/2019 Asfora et al.
2019/0125408 A1 5/2019 Asfora et al.
2019/0133613 A1 5/2019 Reiley et al.
2019/0133769 A1 5/2019 Tetsworth et al.
2019/0133783 A1 5/2019 Unger et al.
2019/0142606 A1 5/2019 Freudenberger
2019/0150910 A1 5/2019 Jones et al.
2019/0151113 A1 5/2019 Sack
2019/0151114 A1 5/2019 Sack
2019/0167314 A1 6/2019 Mosnier et al.
2019/0167326 A1 6/2019 Greenhalgh et al.
2019/0183653 A1 6/2019 Gregersen et al.
2019/0231554 A1 8/2019 Bishop et al.
2019/0239935 A1 8/2019 Willis et al.
2019/0247094 A1 8/2019 Yacoub et al.
2019/0254719 A1 8/2019 Gandhi et al.
2019/0254840 A1 8/2019 Gray et al.
2019/0262048 A1 8/2019 Sutika
2019/0262049 A1 8/2019 Tempco et al.
2019/0290441 A1 9/2019 Tong et al.
2019/0298528 A1 10/2019 Lindsey et al.
2019/0298542 A1 10/2019 Kloss
2019/0328546 A1 10/2019 Palagi et al.
2019/0343564 A1 11/2019 Tempco et al.
2019/0343565 A1 11/2019 Tempco et al.
2019/0343566 A1 11/2019 Tempco et al.
2019/0343567 A1 11/2019 Tempco et al.
2019/0343640 A1 11/2019 Donner et al.

(56) References Cited

U.S. PATENT DOCUMENTS

2019/0343644 A1 11/2019 Ryan et al.
2019/0343645 A1 11/2019 Miccio et al.
2019/0343652 A1 11/2019 Petersheim et al.
2019/0343653 A1 11/2019 McKay
2019/0388131 A1 12/2019 Mehl et al.
2019/0388228 A1 12/2019 Donner et al.
2019/0388242 A1 12/2019 Harris et al.
2020/0000595 A1 1/2020 Jones et al.
2020/0022817 A1 1/2020 Crossgrove et al.
2020/0038069 A1 2/2020 Jones et al.
2020/0046512 A1 2/2020 Newman et al.
2020/0069431 A1 3/2020 Boehm et al.
2020/0093603 A1 3/2020 Manwill et al.
2020/0100822 A1 4/2020 Lipow
2020/0129214 A1 4/2020 Pepper et al.
2020/0138485 A1 5/2020 Kuwamura et al.
2020/0138492 A1 5/2020 Kavanagh
2020/0146721 A1 5/2020 Sadiq
2020/0149137 A1 5/2020 Roth
2020/0170679 A1 6/2020 Sciubba et al.
2020/0206390 A1 7/2020 Roth
2020/0222088 A1 7/2020 Kraus
2020/0222195 A1 7/2020 Assell et al.
2020/0246158 A1 8/2020 Bergey
2020/0246159 A1 8/2020 Suh et al.
2020/0254140 A1 8/2020 Roth
2020/0268449 A1 8/2020 Solitro et al.
2020/0268518 A1 8/2020 Suh et al.
2020/0276019 A1 9/2020 Shetty et al.
2020/0281729 A1* 9/2020 Schifano ............ A61B 17/8875
2020/0297496 A1 9/2020 Mullin
2020/0305896 A1 10/2020 Castro
2020/0315647 A1 10/2020 Fojtik et al.
2020/0315666 A1 10/2020 Nichols et al.
2020/0315669 A1 10/2020 Dejardin
2020/0323563 A1 10/2020 Rezach et al.
2020/0345510 A1 11/2020 Reiley
2020/0375750 A1 12/2020 Abbasi et al.
2020/0397491 A1 12/2020 Frey et al.
2021/0022882 A1 1/2021 Dang et al.
2021/0059834 A1 3/2021 Miguel et al.
2021/0085470 A1 3/2021 Ty
2021/0107093 A1 4/2021 Tempco
2021/0196332 A1 7/2021 Patel
2021/0212833 A1 7/2021 Chin et al.
2021/0228360 A1 7/2021 Hunt et al.
2021/0228363 A1 7/2021 Suddaby
2021/0236146 A1* 8/2021 Donner .............. A61B 17/1604
2021/0244449 A1 8/2021 Castro
2021/0244452 A1 8/2021 Castro
2021/0275233 A1 9/2021 Fang et al.
2021/0338454 A1 11/2021 Afzal
2021/0346038 A1 11/2021 Fiechter et al.
2021/0353337 A1 11/2021 Kaufmann et al.
2021/0353338 A1 11/2021 Meek et al.
2021/0393298 A1 12/2021 Castro
2021/0393408 A1* 12/2021 Ginn .................. A61B 17/1604
2021/0393409 A1 12/2021 Ginn
2021/0401581 A1* 12/2021 Ginn .................. A61B 17/1604
2022/0031365 A1 2/2022 Suh et al.
2022/0273447 A1 9/2022 Ginn
2022/0273448 A1 9/2022 Ginn et al.
2022/0280303 A1 9/2022 Mauldin et al.
2022/0296377 A1 9/2022 Ginn et al.
2022/0296378 A1 9/2022 Ginn
2022/0304672 A1 9/2022 Kalhorn et al.
2022/0304813 A1 9/2022 Ginn et al.
2022/0304814 A1 9/2022 Ginn
2022/0354654 A1 11/2022 Lewis et al.
2022/0361924 A1 11/2022 Castro
2022/0409381 A1 12/2022 Ginn
2023/0000526 A1 1/2023 Follini et al.
2023/0000630 A1 1/2023 Ginn et al.
2023/0000631 A1 1/2023 Ginn et al.
2023/0014384 A1 1/2023 Cordonnier et al.
2023/0025644 A1 1/2023 Maxwell et al.
2023/0032203 A1 2/2023 Maxwell et al.
2023/0039837 A1* 2/2023 Greenhalgh ....... A61B 17/8888
2023/0047553 A1 2/2023 Fauth et al.
2023/0048409 A1 2/2023 Mangone et al.
2023/0049559 A1 2/2023 Fauth et al.
2023/0076180 A1 3/2023 Schifano et al.
2023/0088477 A1 3/2023 Roussouly et al.
2023/0145974 A1 5/2023 Asfora
2023/0165612 A1 6/2023 Castro
2023/0181322 A1* 6/2023 Greenhalgh ....... A61B 17/1659 623/18.11
2023/0181323 A1* 6/2023 Greenhalgh ....... A61B 17/1604 623/18.11
2023/0190442 A1 6/2023 Castro
2023/0210667 A1 7/2023 Lindsey et al.
2023/0248392 A1 8/2023 Whittaker et al.
2023/0248886 A1 8/2023 Roth et al.
2023/0255670 A1 8/2023 Castro
2023/0263553 A1 8/2023 Compton et al.
2023/0270559 A1 8/2023 Mesiwala et al.
2023/0277723 A1 9/2023 Roth
2023/0285054 A1 9/2023 Mehl et al.
2023/0285156 A1 9/2023 Sansur et al.
2023/0293206 A1 9/2023 Mundis et al.
2023/0301665 A1 9/2023 Aksu
2023/0321317 A1 10/2023 Suh
2023/0329765 A1 10/2023 Lavigne et al.
2023/0355408 A1 11/2023 Freeman et al.
2023/0363927 A1 11/2023 LaNeve et al.
2023/0390078 A1* 12/2023 Bergey .................. A61F 2/4455
2023/0404762 A1* 12/2023 Ginn .................. A61B 17/1664
2024/0002983 A1 1/2024 Roth et al.
2024/0008901 A1 1/2024 Roth et al.
2024/0032975 A1* 2/2024 Loftus ................ A61B 17/3472
2024/0050131 A1 2/2024 Bannigan et al.
2024/0065734 A1 2/2024 Rezach
2024/0065767 A1 2/2024 Cordonnier et al.
2024/0081870 A1 3/2024 Castro
2024/0081873 A1 3/2024 Gilbride
2024/0091026 A1 3/2024 Arnold et al.
2024/0108414 A1 4/2024 Dreyer et al.
2024/0108469 A1 4/2024 Raji et al.
2024/0115398 A1 4/2024 Frey et al.
2024/0122627 A1 4/2024 Kinzner et al.
2024/0138890 A1 5/2024 Jordan et al.
2024/0148328 A1 5/2024 Fedon et al.
2024/0148422 A1 5/2024 Solitro et al.
2024/0148510 A1 5/2024 Sprick et al.
2024/0150872 A1 5/2024 Roth
2024/0157031 A1 5/2024 Yadav et al.
2024/0173146 A1* 5/2024 Greenhalgh ....... A61B 17/1615
2024/0175110 A1 5/2024 Roth
2024/0180595 A1 6/2024 Robbins
2024/0180707 A1 6/2024 Peretz et al.
2024/0188996 A1 6/2024 Frock et al.
2024/0189108 A1 6/2024 Moseley et al.
2024/0189109 A1 6/2024 Moseley et al.
2024/0197956 A1 6/2024 Bauman et al.
2024/0197957 A1 6/2024 Roth et al.
2024/0206885 A1 6/2024 Sand et al.
2024/0225667 A9 7/2024 Reiley et al.
2024/0225856 A1 7/2024 Castro
2024/0238019 A1 7/2024 Alabdulrahman et al.
2024/0252717 A1 8/2024 Suh et al.
2024/0254597 A1 8/2024 Roth
2024/0261011 A1 8/2024 LaNeve et al.
2024/0261107 A1 8/2024 Ginn et al.
2024/0285410 A1 8/2024 Ginn et al.
2024/0366401 A1* 11/2024 Bergey .................. A61F 2/4611
2024/0374388 A1 11/2024 Kowalski
2024/0374399 A1 11/2024 Stuart et al.
2024/0390048 A1 11/2024 Russell et al.
2024/0390151 A1* 11/2024 Ginn .................. A61B 17/7074
2024/0398453 A1 12/2024 Mauldin et al.
2024/0407810 A1 12/2024 Mesiwala et al.
2024/0407811 A1 12/2024 Hua et al.
2024/0415547 A1 12/2024 Wentz et al.
2024/0415663 A1 12/2024 Gehrchen et al.

(56) References Cited

U.S. PATENT DOCUMENTS

| | | | | |
|---|---|---|---|---|
| 2025/0000657 | A1 | 1/2025 | Sansur et al. | |
| 2025/0009396 | A1 | 1/2025 | Vestgaarden | |
| 2025/0009520 | A1 | 1/2025 | Moseley et al. | |
| 2025/0017638 | A1 | 1/2025 | Bergey | |
| 2025/0025214 | A1 | 1/2025 | Widmer et al. | |
| 2025/0025215 | A1 | 1/2025 | Widmer et al. | |
| 2025/0025216 | A1 | 1/2025 | Mesiwala et al. | |
| 2025/0025309 | A1 | 1/2025 | Casey | |
| 2025/0025310 | A1 | 1/2025 | Greenhalgh et al. | |
| 2025/0040972 | A1 | 2/2025 | Schneider et al. | |
| 2025/0041064 | A1* | 2/2025 | Cuevas | A61F 2/30988 |
| 2025/0057547 | A1 | 2/2025 | Spitler et al. | |
| 2025/0073039 | A1 | 3/2025 | Meyer et al. | |
| 2025/0073045 | A1 | 3/2025 | El-Naggar | |
| 2025/0095864 | A1 | 3/2025 | Hanratty et al. | |
| 2025/0099135 | A1 | 3/2025 | Buse | |
| 2025/0099140 | A1* | 3/2025 | Palmer | A61B 17/68 |
| 2025/0099259 | A1 | 3/2025 | Cordaro | |
| 2025/0099263 | A1 | 3/2025 | Seaman et al. | |
| 2025/0099647 | A1 | 3/2025 | Roth et al. | |
| 2025/0107829 | A1 | 4/2025 | McQuinn et al. | |
| 2025/0161070 | A1* | 5/2025 | Sand | A61F 2/4603 |
| 2025/0177011 | A1 | 6/2025 | Stuart et al. | |
| 2025/0177168 | A1* | 6/2025 | Reckling | A61B 17/68 |
| 2025/0268630 | A1 | 8/2025 | Fauth et al. | |
| 2025/0268658 | A1 | 8/2025 | Benson et al. | |
| 2025/0268721 | A1 | 8/2025 | Levine | |
| 2025/0281204 | A1 | 9/2025 | Messerli et al. | |
| 2025/0281213 | A1 | 9/2025 | Frey et al. | |
| 2025/0288331 | A1 | 9/2025 | Fang et al. | |
| 2025/0288336 | A1 | 9/2025 | Harris et al. | |
| 2025/0295437 | A1 | 9/2025 | Baynham | |
| 2025/0318936 | A1 | 10/2025 | Winston et al. | |
| 2025/0339156 | A1 | 11/2025 | Vestgaarden | |
| 2025/0339184 | A1 | 11/2025 | Hynes et al. | |
| 2025/0339188 | A1 | 11/2025 | Fauth et al. | |
| 2025/0352696 | A1 | 11/2025 | Borden | |
| 2025/0359896 | A1 | 11/2025 | Fojtik et al. | |
| 2025/0366867 | A1* | 12/2025 | Mauldin | A61B 17/0218 |
| 2025/0366996 | A1 | 12/2025 | Geist et al. | |
| 2026/0000521 | A1 | 1/2026 | Baynham | |
| 2026/0007419 | A1 | 1/2026 | Reiley et al. | |
| 2026/0007432 | A1 | 1/2026 | Rodriguez Olaverri et al. | |
| 2026/0007471 | A1 | 1/2026 | Winston et al. | |
| 2026/0007528 | A1* | 1/2026 | Schifano | A61F 2/4611 |
| 2026/0009107 | A1 | 1/2026 | Roth et al. | |
| 2026/0013909 | A1 | 1/2026 | Chin et al. | |
| 2026/0020966 | A1 | 1/2026 | Troxell et al. | |
| 2026/0033872 | A1 | 2/2026 | Lewis et al. | |
| 2026/0041567 | A1 | 2/2026 | Spann | |
| 2026/0047870 | A1 | 2/2026 | Hills | |
| 2026/0060730 | A1 | 3/2026 | Moses et al. | |
| 2026/0060809 | A1 | 3/2026 | Sazy | |
| 2026/0069325 | A1 | 3/2026 | Haller et al. | |
| 2026/0069421 | A1 | 3/2026 | Cuevas | |
| 2026/0070124 | A1 | 3/2026 | Roth | |
| 2026/0077096 | A1 | 3/2026 | Roth | |
| 2026/0077097 | A1 | 3/2026 | Roth | |
| 2026/0083481 | A1 | 3/2026 | Follini et al. | |
| 2026/0083483 | A1 | 3/2026 | Simpson et al. | |
| 2026/0083489 | A1 | 3/2026 | Black et al. | |
| 2026/0083875 | A1 | 3/2026 | Roth | |
| 2026/0090872 | A1 | 4/2026 | Stuart et al. | |
| 2026/0096836 | A1 | 4/2026 | Peretz | |

FOREIGN PATENT DOCUMENTS

| | | | |
|---|---|---|---|
| CN | 1909848 | A | 2/2007 |
| CN | 101795632 | A | 8/2010 |
| CN | 102361601 | A | 2/2012 |
| CN | 102429716 | A | 5/2012 |
| CN | 104968283 | A | 10/2015 |
| CN | 109124748 | A | 6/2017 |
| DE | 102011001264 | A1 | 9/2012 |
| DE | 102012106336 | A1 | 1/2014 |
| EP | 1287796 | A1 | 3/2003 |
| EP | 2070481 | B1 | 2/2012 |
| EP | 2796104 | A1 | 10/2014 |
| EP | 2590576 | B1 | 10/2015 |
| EP | 2749238 | B1 | 3/2017 |
| EP | 2887899 | B1 | 8/2017 |
| EP | 2341852 | B1 | 8/2018 |
| EP | 2496162 | B1 | 10/2018 |
| EP | 3484387 | A1 | 5/2019 |
| EP | 3501457 | A1 | 6/2019 |
| EP | 356044/8 | A1 | 10/2019 |
| EP | 3593745 | A2 | 1/2020 |
| EP | 3616634 | A1 | 3/2020 |
| EP | 3661441 | A1 | 6/2020 |
| EP | 2328495 | B1 | 7/2020 |
| EP | 2408389 | B1 | 4/2021 |
| JP | 59200642 | A | 11/1984 |
| JP | 05-176942 | A | 7/1993 |
| JP | 05184615 | A | 7/1993 |
| JP | 09149906 | A | 10/1997 |
| JP | 10-85231 | A | 4/1998 |
| JP | 11318931 | A | 11/1999 |
| JP | 2002509753 | A | 4/2002 |
| JP | 2003511198 | A | 3/2003 |
| JP | 2003533329 | A | 11/2003 |
| JP | 2003534046 | A | 11/2003 |
| JP | 2004121841 | | 4/2004 |
| JP | 2004512895 | | 4/2004 |
| JP | 2004516866 | | 6/2004 |
| JP | 2006506181 | | 2/2006 |
| JP | 2007535973 | A | 12/2007 |
| JP | 2008540036 | A | 11/2008 |
| JP | 2009000501 | A | 1/2009 |
| JP | 2009521990 | A | 6/2009 |
| JP | 2009533159 | A | 9/2009 |
| JP | 2010137016 | A | 6/2010 |
| JP | 2011041802 | A | 3/2011 |
| JP | 2011512939 | A | 4/2011 |
| JP | 2012030105 | A | 2/2012 |
| JP | 2014000402 | A | 1/2014 |
| JP | 2014147820 | A | 8/2014 |
| JP | 2015510506 | A | 4/2015 |
| JP | 2015171520 | A | 10/2015 |
| JP | 2015531282 | A | 11/2015 |
| JP | 2016515857 | A | 6/2016 |
| JP | 2017528251 | A | 9/2017 |
| JP | 2017533759 | A | 11/2017 |
| JP | 2019506993 | A | 3/2019 |
| KR | 102537768 | B1 | 5/2023 |
| WO | WO97/31517 | A2 | 8/1997 |
| WO | WO01/17445 | A1 | 3/2001 |
| WO | WO02/38054 | | 5/2002 |
| WO | WO03/007839 | A2 | 1/2003 |
| WO | WO04/02344 | | 1/2004 |
| WO | WO2004/043277 | A1 | 5/2004 |
| WO | WO2005/009729 | A2 | 2/2005 |
| WO | WO2006/003316 | | 1/2006 |
| WO | WO2006/023793 | A2 | 3/2006 |
| WO | WO2006/074321 | A2 | 7/2006 |
| WO | WO2006/116850 | A1 | 11/2006 |
| WO | WO2008/153723 | A1 | 12/2008 |
| WO | WO2009/025884 | A2 | 2/2009 |
| WO | WO2009/029074 | A1 | 3/2009 |
| WO | WO2010/105196 | A1 | 9/2010 |
| WO | WO2011/010463 | A1 | 1/2011 |
| WO | WO2011/110865 | A2 | 9/2011 |
| WO | WO2011/124874 | A1 | 10/2011 |
| WO | WO2011/149557 | A1 | 12/2011 |
| WO | WO2012/015976 | A1 | 2/2012 |
| WO | WO2012/048008 | A1 | 4/2012 |
| WO | WO2013/000071 | A1 | 1/2013 |
| WO | WO2013/052807 | A2 | 4/2013 |
| WO | WO2013/119907 | A1 | 8/2013 |
| WO | WO2013/134678 | A1 | 9/2013 |
| WO | WO2014/145902 | A1 | 9/2014 |
| WO | WO2017/147140 | A1 | 8/2017 |
| WO | WO2017/147537 | A1 | 8/2017 |
| WO | WO2017/201371 | A1 | 11/2017 |
| WO | WO2019/152737 | A1 | 8/2019 |

(56) References Cited

FOREIGN PATENT DOCUMENTS

| | | | | | |
|---|---|---|---|---|---|
| WO | WO2020/168269 | A1 | | 8/2020 | |
| WO | WO2021/168269 | A1 | | 8/2021 | |
| WO | WO2022/125619 | A1 | | 6/2022 | |
| WO | WO2023/235789 | A2 | | 12/2023 | |
| WO | WO2024/151594 | A1 | | 7/2024 | |
| WO | WO-2024254613 | A1 | * | 12/2024 | ......... A61F 2/20988 |
| WO | WO2025/038769 | A1 | | 2/2025 | |
| WO | WO2025/193873 | A1 | | 9/2025 | |

OTHER PUBLICATIONS

Reckling et al; U.S. Appl. No. 18/809,229 entitled “Sacro-iliac joint stabilizing implants and methods of implantation,” filed Aug. 19, 2024.

Mesiwala et al.; U.S. Appl. No. 18/810,211 entitled “Implants for spinal fixation and or fusion,” filed Aug. 20, 2024.

Sand et al.; U.S. Appl. No. 18/951,349 entitled “Systems, devices, and methods for preparing bone to receive an implant,” filed Nov. 18, 2024.

Acumed; Acutrak Headless Compressioin Screw (product information); 12 pgs; ©2005; retrieved Sep. 25, 2014 from http://www.rosed.ac.uk/fellows/lvanrensburg/classification/surgtech/acumed/manuals/acutrak-brochure%200311.pdf.

Al-Khayer et al.; Percutaneous sacroiliac joint arthrodesis, a novel technique; J Spinal Disord Tech; vol. 21; No. 5; pp. 359-363; Jul. 2008.

Eisner; New SI Joint Fusion System Cleared; Orthopedics This Week; Jun. 28, 2018; retreived from the internet <https://ryortho.com/breaking/new-si-joint-fusion-system-cleared/> on Sep. 8, 2022; 5 pages.

Khurana et al.; Percutaneous fusion of the sacroiliac joint with hollow modular anchorage screws, clinical and radiological outcome; J Bone Joint Surg; vol. 91-B; No. 5; pp. 627-631; May 2009.

Lu et al.; Mechanical properties of porous materials; Journal of Porous Materials; 6(4); pp. 359-368; Nov. 1, 1999.

Peretz et al.; The internal bony architecture of the sacrum; Spine; 23(9); pp. 971-974; May 1, 1998.

Richards et al.; Bone density and cortical thickness in normal, osteopenic, and osteoporotic sacra; Journal of Osteoporosis; 2010(ID 504078); 5 pgs; Jun. 9, 2010.

Thiesen et at.; The three-dimensional bone mass distribution of the posterior pelvic ring and its key role in transsacral screw placement; Scientific Reports; 10(1); doi.org/10.1038/s41598-020-61954-8; 8 pages; Mar. 2020.

Third Party Observation; PCT/US2021/062337; Aug. 29, 2022; 6 pages.

Wise et al; Minimally invasive sacroiliac arthrodesis, outcomes of a new technique; J Spinal Disord Tech; vol. 21; No. 8; pp. 579-584; Dec. 2008.

Anderson Jr et al.; U.S. Appl. No. 18/870,896 entitled “Bi-lateral pelvic stabilization,” filed Dec. 2, 2024.

Polly et al.; U.S. Appl. No. 19/024,752 entitled “Spine stabilization,” filed Jan. 16, 2025.

Follini et al.; U.S. Appl. No. 19/078,206 entitled “Threaded bone implant and systems,” filed Mar. 12, 2025.

Mesiwala et al.; U.S. Appl. No. 19/349,840 entitled “Fusion cages and methods for sacro-iliac joint stabilization,” filed Oct. 3, 2025.

Lindsey et al.; U.S. Appl. No. 19/317,804, entitled Threaded implants and methods of use across bone segments, filed Sep. 3, 2025.

* cited by examiner

FIG. 22
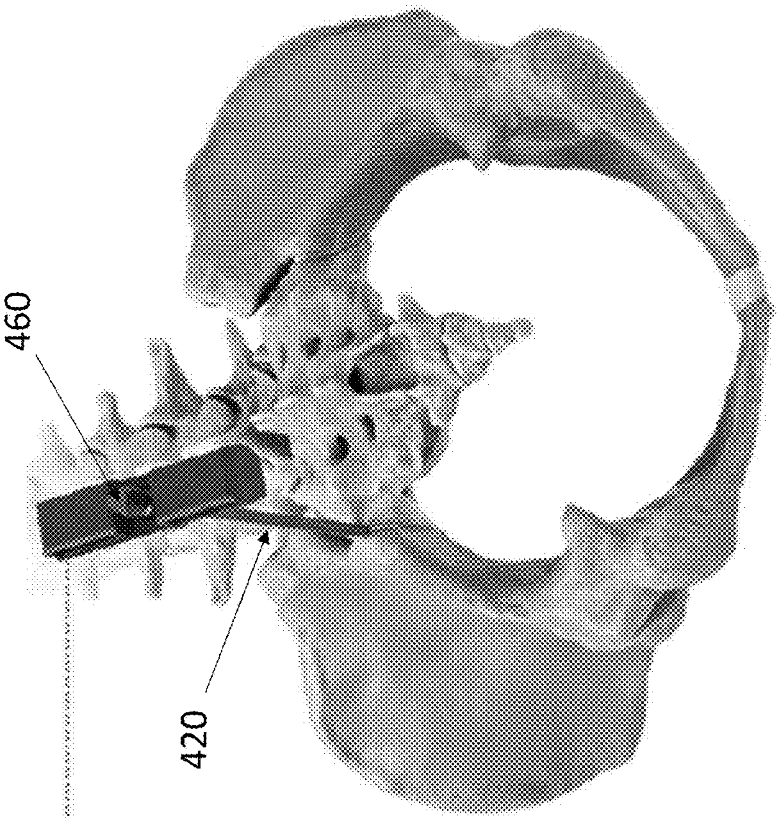
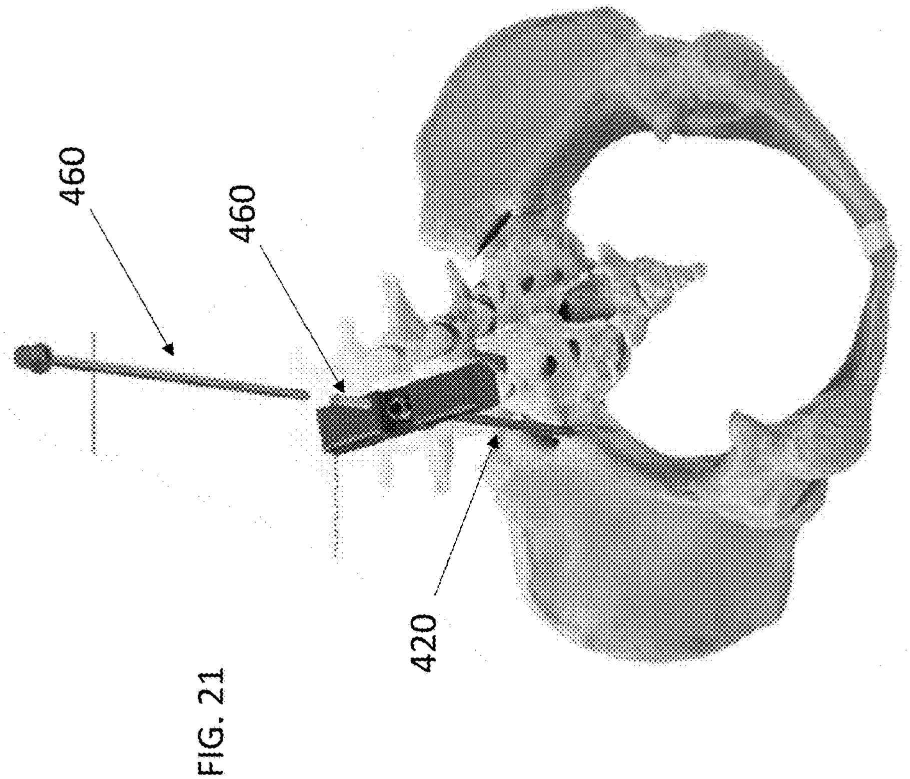
FIG. 21

SACROILIAC JOINT STABILIZATION, INCLUDING IMPLANTS, SYSTEMS AND METHODS OF DELIVERING IMPLANTS

CROSS REFERENCE TO RELATED APPLICATIONS

This application claims the benefit of U.S. Provisional App. No. 63/600,475, filed Nov. 17, 2023, which is fully incorporated by reference herein for all purposes.

INCORPORATION BY REFERENCE

All publications and patent applications mentioned in this specification are herein incorporated by reference to the same extent as if each individual publication or patent application was specifically and individually indicated to be incorporated by reference.

BACKGROUND

It would be beneficial for SI joint implantation procedures to require fewer instruments, tools and steps than existing procedures, particularly for dorsal, down-the-joint, deliveries, and particularly for bone dowel implants.

SUMMARY OF THE DISCLOSURE

One aspect of the disclosure is a method of positioning a sacroiliac (SI) joint implant, comprising: in a dorsal trajectory, positioning a stylet removably coupled with a cannula adjacent to an SI joint, the stylet disposed through a cannula lumen with sharp distal tip of the stylet 20 mm-40 mm distally from a cannula distal end; advancing, in the dorsal trajectory, the sharp distal end of the stylet down and into an SI joint, while a portion of the stylet is within the cannula lumen, to disrupt the SI joint and prepares the SI joint to receive an SI joint implant; removing the stylet from the SI joint and from the cannula lumen, leaving the cannula distal end adjacent to the SI joint; positioning an SI joint implant into the cannula lumen; advancing the SI joint implant with a plunger distally through the cannula lumen and into the SI joint; removing the plunger from the cannula; and removing the cannula from the subject while leaving the implant in the SI joint.

One aspect of the disclosure is a method of positioning a sacroiliac (SI) joint implant, comprising: advancing, in a dorsal approach, a cannula to a level of an SI joint; advancing a sharp distal end of a stylet down the SI joint while a portion of the stylet is within a cannula lumen, wherein a distal tip of the stylet is positioned 20 mm-40 mm distally from a cannula distal end, and wherein advancing the sharp distal end of the stylet down the SI joint disrupts the SI joint and prepares the SI joint to receive an SI joint implant; removing the stylet from the cannula lumen and leaving the cannula adjacent to the SI joint; positioning an SI joint implant into the cannula lumen; advancing the SI joint implant distally through the cannula lumen and down and into the SI joint; and removing the cannula from the subject while leaving the implant in the patient.

One aspect of the disclosure is a system for implanting a sacroiliac (SI) joint implant down the SI joint in a dorsal approach, comprising: a cannula having a lumen and a sharpened stylet removably couplable to the cannula, the cannula and stylet are each sized and configured such that, when coupled, a portion of the stylet is within the cannula lumen and a distal tip is 20 mm to 40 mm distal to a distal end of the cannula.

One aspect of the disclosure is a cannula stabilization and stylet removal tool, comprising: an elongate body adapted to be held by a hand of an operator; a clamp end comprising a first jaw movable relative to a second jaw about a pivot, the first jaw including a first locking element; a locking collar axially movable relative to the elongate body, the locking collar including a second locking element sized and configured to interface with the first locking element to maintain the collar in a locked position relative to the elongate body and prevent clamp ends of the first and second jaws from moving away from one another; and a lever end opposite the clamp end, the lever end comprising first and second hooks each having a curved configuration including a recessed surface, the curved first and second hooks extending from the elongate body, and each of the first and second hooks sized and configured to accommodate and interface with a proximal handle portion of a stylet to facilitate application of a removal force to the proximal handle portion of the stylet.

BRIEF DESCRIPTION OF THE DRAWINGS

FIG. 21 illustrates positioning an implant into a cannula lumen followed by a tamp.

FIG. 22 illustrates advancing a tamp to distally advance the implant.

DETAILED DESCRIPTION

There may be a need to stabilize and/or fuse one or more of a subject's sacroiliac (SI) joints. Methods herein include methods of delivering stabilizing and/or fusing implants to the SI joint, wherein when implanted stabilize the implant over time. The terms stabilizing and fusing (and derivatives thereof) may both be referred to herein as "stabilizing" or "stabilization" (or derivatives thereof). Implant procedures herein describe dorsal, or posterior, approaches for accessing, preparing the joint, and delivering the implant, all of which are considered herein as dorsal approaches. The dorsal approaches described herein comprise delivering implants "down the joint." Implants herein may also be described as being implanted in a dorsal or posterior manner. The entire disclosure of US20230000639A1, including dorsal/posterior approaches and trajectories is incorporated by reference herein and may be used at least in part in the dorsal approaches and trajectories for delivering the SI joint implants herein.

Figure 1:
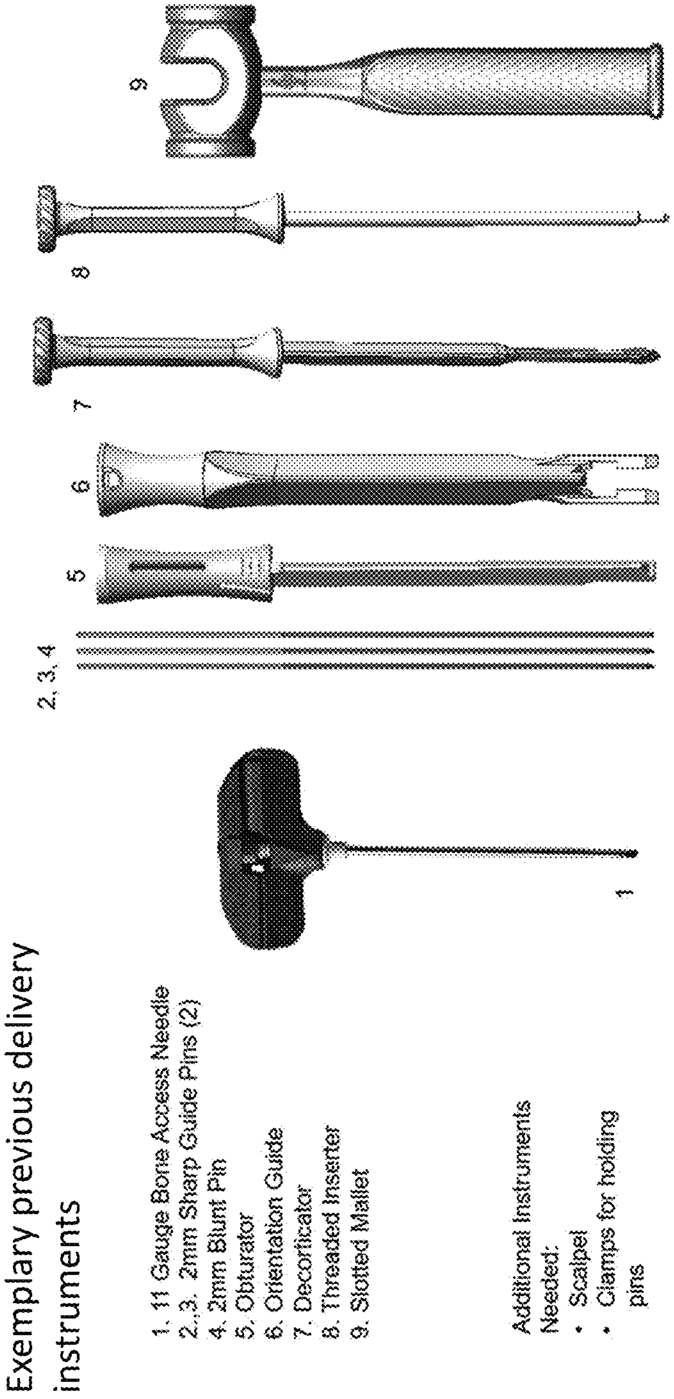
FIG. 1 illustrates a prior art set of instruments, including more components and complexity that approaches and instrument sets herein.

One of the advantages of the implantation methods, system, and devices described herein is that they require fewer steps and fewer delivery components compared to other SI joint stabilization procedures that utilize a dorsal, "down the joint" approach. Reducing the number of components and steps shortens the procedure time, reduces the likelihood of component malfunction, reduces the risk of patient injury, reduces cost, and requires less training. For example, methods herein eliminate the need to utilize an obturator, and orientation or placement guide, and/or a decorticator, for example, examples of which are illustrated in FIG. 1.

Figure 15B:
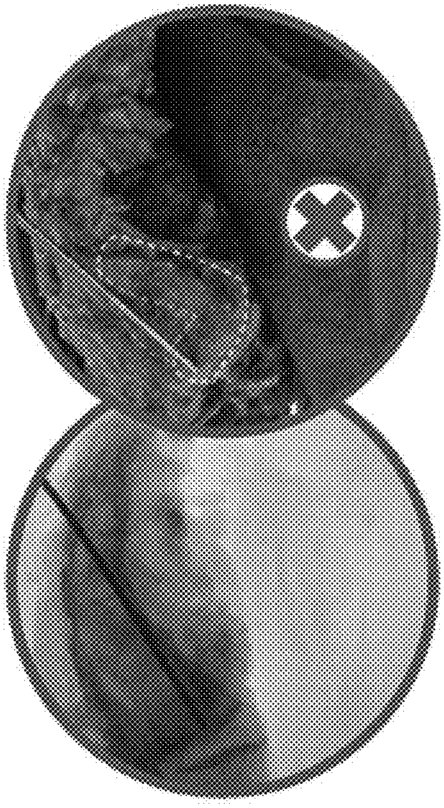
FIG. 15A illustrates a preferred trajectory and position, compared with FIG. 15B.
Figure 15A:
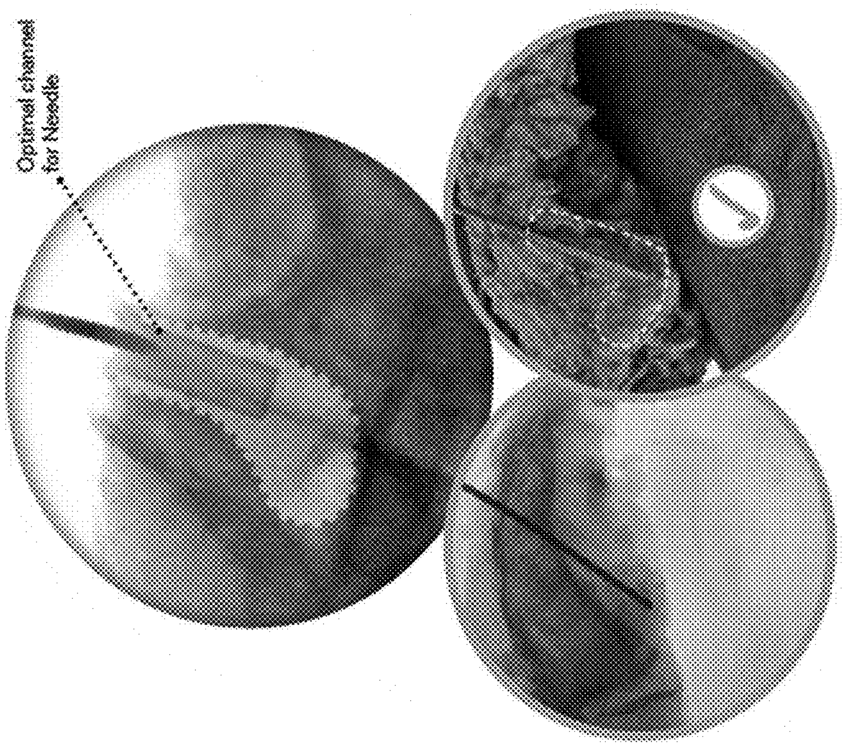

An additional non-limiting advantage of the innovative dorsal approaches and systems described herein is that the trajectory is slightly different than previous dorsal approaches. For example, trajectories herein are inferior, or lower than, previous approaches, as example of which is shown in the preferred trajectory of FIG. 15A compared with the non-preferred trajectory shown in FIG. 15B. FIG. 15B illustrates a less than preferred trajectory, which is more superior compared with the trajectory illustrated in FIG. 15A, and which passes through, or includes a higher probability of passing through, the ligamentous portion of the SI joint. Any of the methods herein that advance a sharpened stylet down the joint may therefore include advancing the stylet in the trajectory shown in FIG. 15A, which is through the articular portion of the joint rather than the ligamentous portion of the joint. The trajectory shown in FIG. 15A is also referred to as being aligned with the ventral aspect of the articular joint. The trajectory shown in FIG. 15A (which is the same trajectory for pain injections, so which may be more familiar to physicians) may provide for better bone seating and anchoring when the implant is implanted.

While the disclosure herein focuses on dorsal approach, methods and systems described herein may find application in lateral implantation methods, wherein the implant is implanted laterally across the SI joint, across an ilium, across the SI joint, and into the sacrum.

Figure 2:
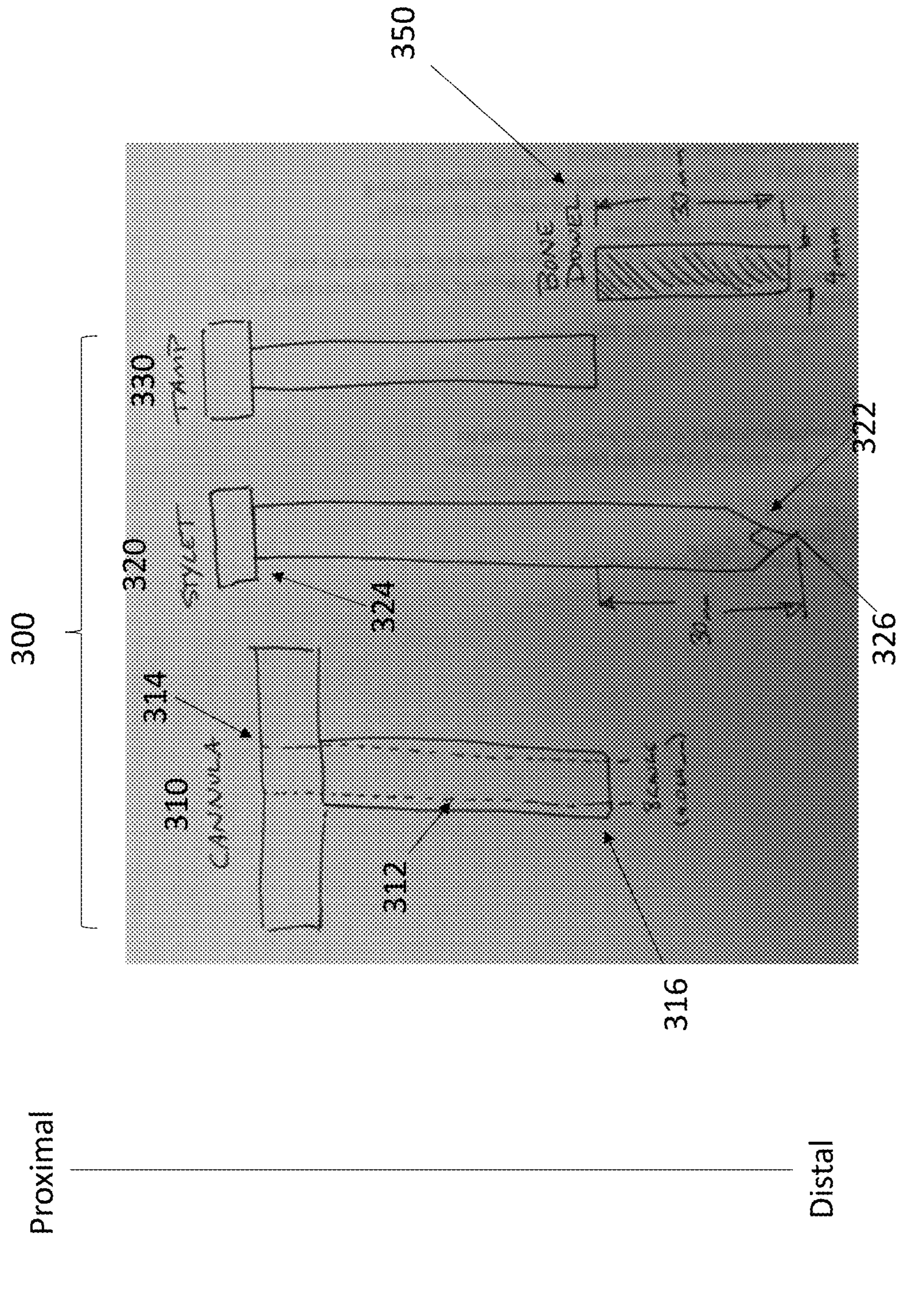
FIG. 2 illustrates an exemplary set of instruments for delivering an SI joint implant.

FIG. 2 illustrates exemplary instruments 300 for one or more of accessing an SI joint, preparing an SI joint for an implant, and delivering an implant down the SI joint. Relative proximal and distal directions are labeled. Instruments 300 include cannula 310 with internal lumen 312 therethrough from a proximal end to distal end 316; stylet 320 with a sharpened distal end sized and configured to be disposed within and removable from cannula lumen 312, with a sharpened distal end 322 for entry into and down the SI joint to prepare the SI joint for the implant; and an implant plunger or tamp 330 sized and configured to (after the stylet is removed from cannula lumen 312) advancing (optionally pushing distally) the implant 350 distally through cannula lumen 312 and into the SI joint.

FIG. 2 illustrates an exemplary SI joint stabilization implant or bone dowel 350, with exemplary and non-limiting dimensions provided, which is configured to be advanced distally through cannula lumen 312 and into an SI joint.

Figure 3:
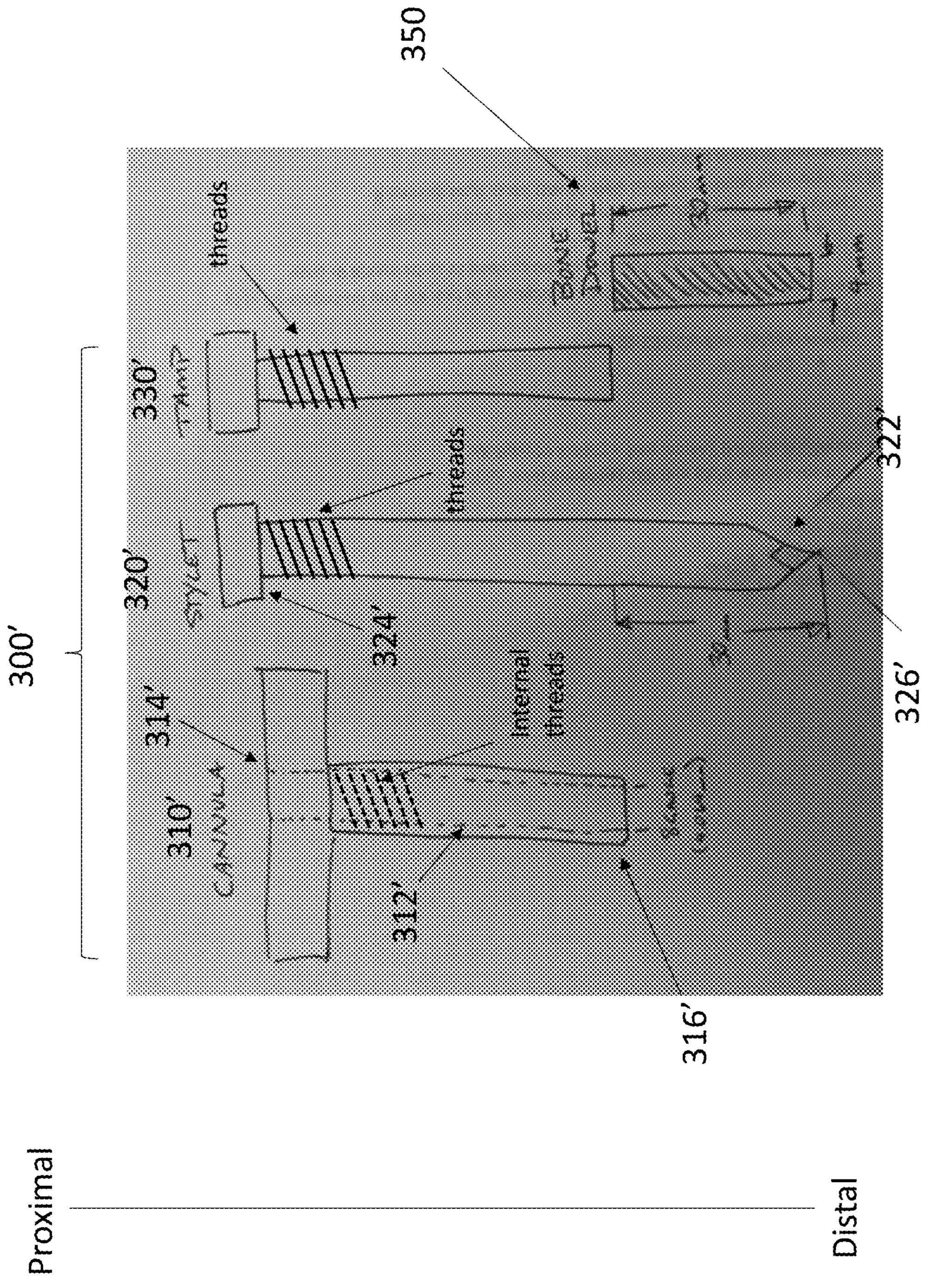
FIG. 3 illustrates an exemplary set of instruments for delivering an SI joint implant.

FIG. 3 illustrates alternative instruments 300' with components labeled similarly as in the system of FIG. 2. The stylets herein can be removably coupled to the cannulas herein in a variety of ways. For example, the stylets herein may optionally have outer threads shaped to mate with inner threads on the cannula lumen, such as shown in FIG. 3. This arrangement can allow the stylet to be removed by rotating the stylet relative to the cannula, compared with an axially directed proximal pulling force out of the SI joint, which is described with systems below. The stylets herein may also include at least one proximal region surface (e.g., surface 324'), and the cannula may include at least one proximal end surface (e.g., surface 314'), wherein the at least one proximal end surfaces on the stylet and the cannula are sized and configured to engage to prevent further distal stylet movement and maintain the relative distal positions of the cannula and the stylet when engaged, which may cause the distal tip (e.g., 326') of the stylet to be 20 mm-40 mm distally beyond a cannula distal end.

Similarly, the plungers described herein may have outer threads sized and configured to interface with a cannula lumen inner threads, such as shown in FIG. 3, which may facilitate advancing the implant upon rotation of the plunger relative to the cannula (and to retract the plunger).

Figure 4:
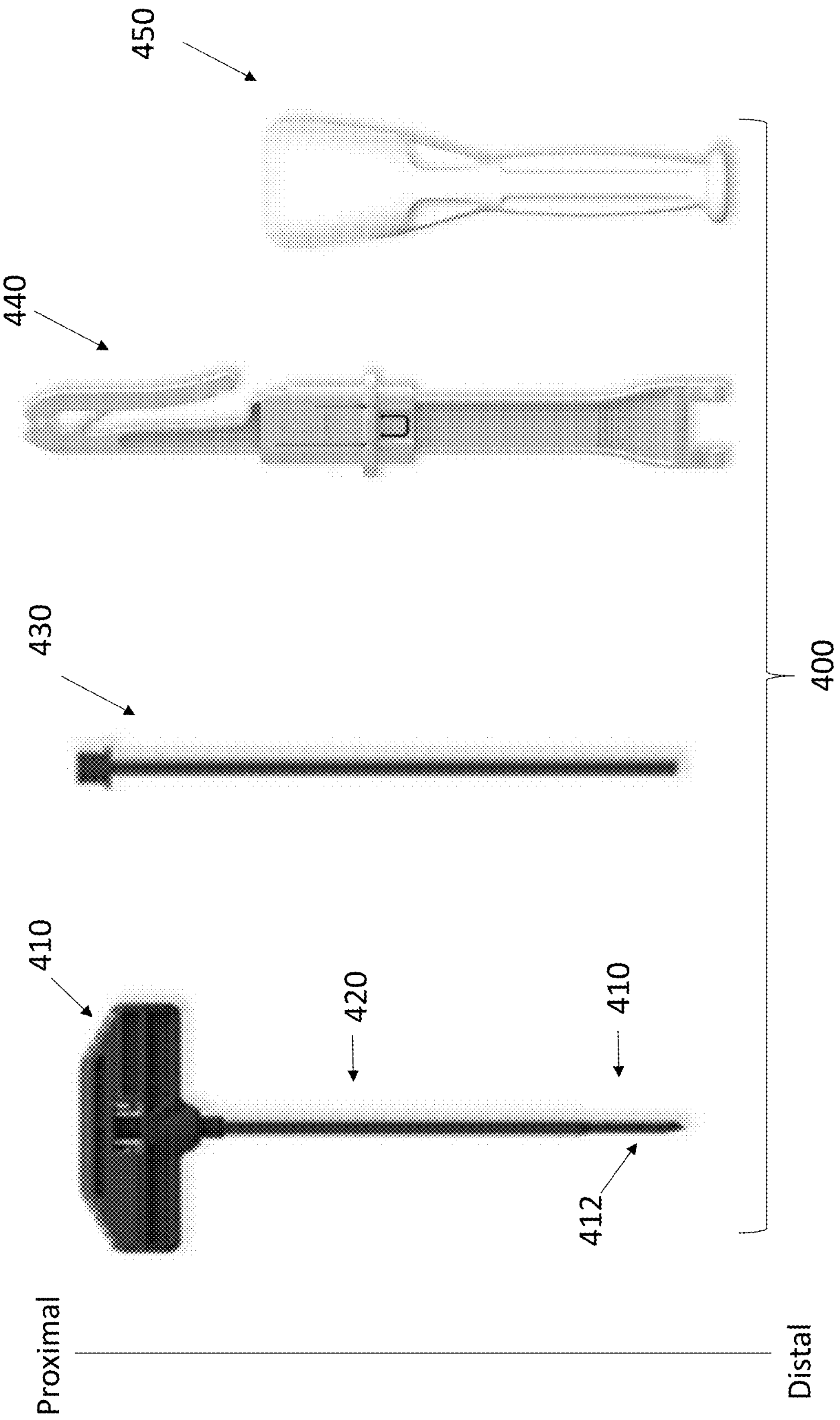
FIG. 4 illustrates an exemplary set of instruments for delivering an SI joint implant.
Figure 6A:
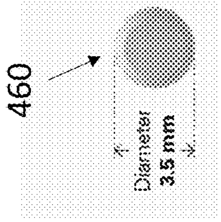
FIGS. 6A and 6B illustrate an exemplary SI joint implant.
Figure 6B:
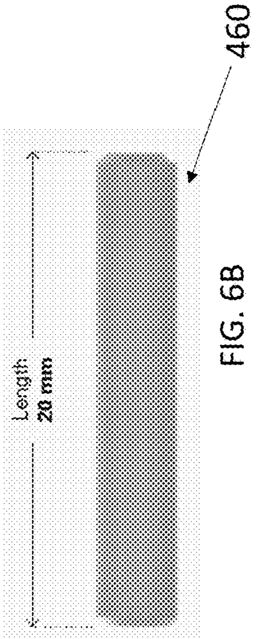

FIG. 4 illustrates an alternative system of instruments 400 that includes stylet 410, cannula 420, tamp or plunger 430, optional stabilization and lever tool 440, and mallet 450. An implant 460 that may be implanted with system 400 is shown in the end view of FIG. 6A and side view of FIG. 6B, although other implants may be implanted with system 400. Stylet 410 is shown within cannula 420, with the distal region 412 of stylet shown extending distally beyond the distal end of cannula. Use of instruments 400 is described in more detail herein. When the stylet is positioned within the cannula (e.g., as in FIG. 4), the stylet and cannula may be referred to herein as, for example, "integrated," "combined," "assembled" and/or may together be referred to as a "needle."

Figure 5B:
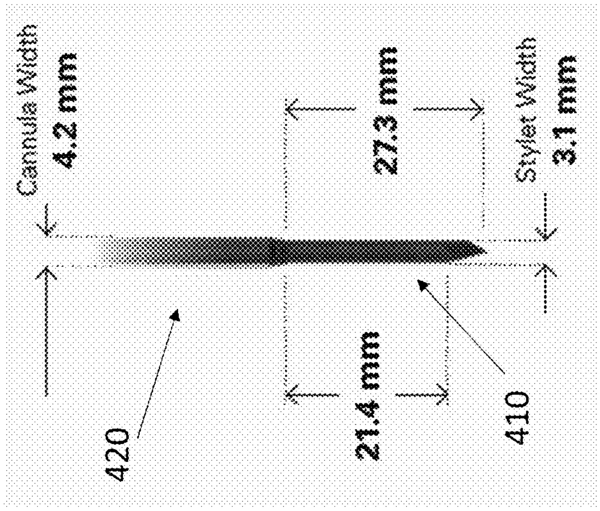
FIGS. 5A and 5B illustrate an exemplary integrated cannula and stylet.
Figure 5A:
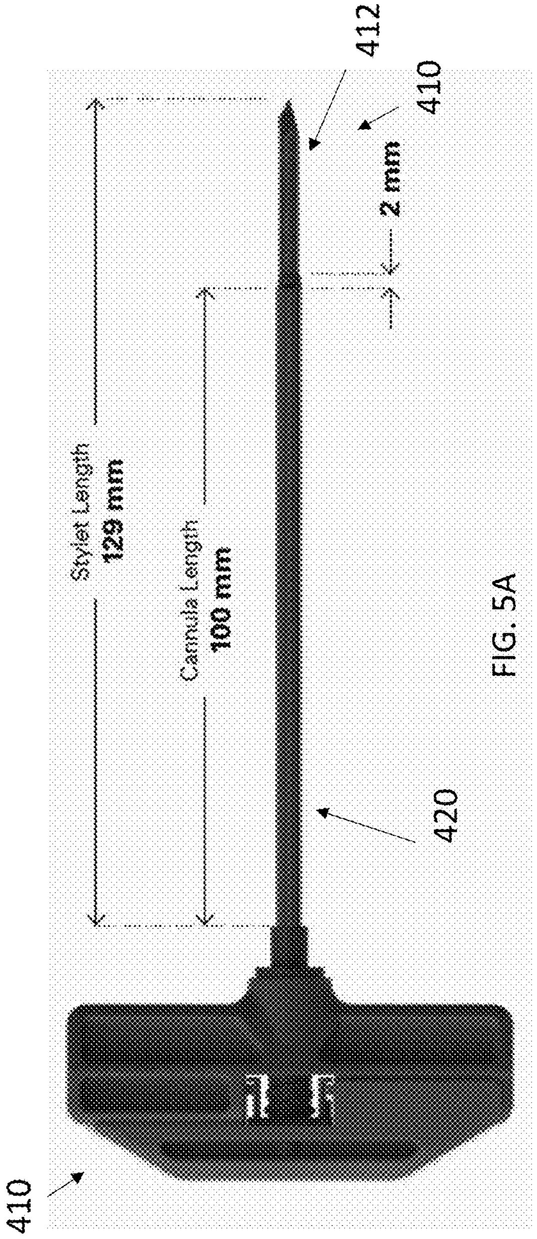

Additional exemplary and non-limiting features of stylet and cannula are shown in FIGS. 5A and 5B, where FIG. 5B illustrates a distal portion of the combined cannula and stylet.

The stylets described herein have a length that is greater than a length of the corresponding cannula in which the stylet is disposed. The stylets described herein have a sharp or sharpened distal end (e.g., distal end 322) that includes a distal tip (e.g., distal tip 326), wherein the distal tip is the furthest distal location on the stylet. The lengths are measure proximal to distal, with exemplary lengths labeled in FIG. 5A for reference. In general, the stylets herein prepare the joint for the implant (e.g., bone dowel). The stylets herein may have a smooth outer surface. Alternatively, the stylets herein may include one or more abrasive and/or rasping elements on an outer surface thereof that are adapted to further disrupt the SI joint (further disrupt considered relative to the sharped distal end).

Figure 7:
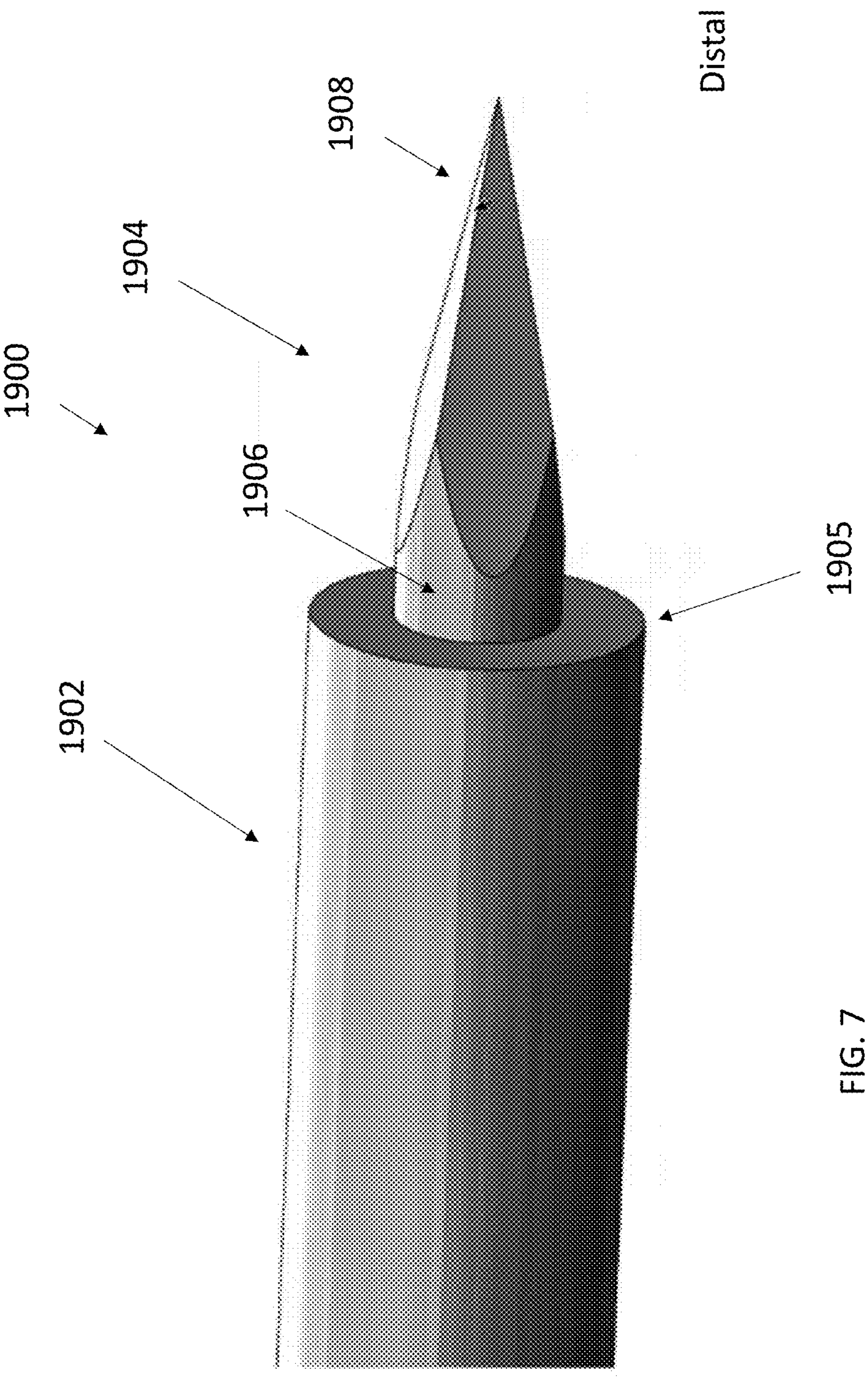
FIG. 7 illustrates an exemplary distal region of an exemplary stylet.

FIG. 7 illustrates an exemplary alternative stylet 1900, which may be used with and/or integrated into any of the instruments herein. As shown, the distal end of the stylet 1900 includes a region with step 1905, so the square (or other step which may have a non-90 degree angle) shoulder of step 1905 is adapted to, and will when advanced, scrape cartilage down the joint, so that the implant can be implanted against bleeding bone. Tip 1906 may optionally be 2 mm in diameter with a 15 degree 4-sided trocar 1908.

Plungers or tamps described herein (e.g., plungers 330, 430) are generally sized and configured to fit within the cannula lumen and advance the implant therethrough, optionally upon a proximal force applied to the plunger (e.g., with a mallet) and indirectly to the implant through the plunger.

The SI joint implants described herein may have a variety of sizes and configurations. The implants may have a cylindrical configuration, optionally with short bevels at one or both of the implant ends (e.g., as with implant 460). Cylindrically configured implants may be easier to manufacture than other configurations. The implants may have oval, or square (or other rectilinear) cross sectional shapes (in a plane transverse to the implant long axis).

The implants herein may be sized to be implanted solely in the SI joint, or they may be sized and configured to be implanted such that they extend into the sacral and/or iliac bones adjacent the SI joint to some extent.

The implants herein may have smooth outer surfaces. The implants herein may have porous outer surfaces, which are optionally coatings or a result of a manufacturing process.

The implants herein may have the same outer diameter ("OD") as the stylet. The implants herein may have an OD greater than or less than the OD of the stylet. The implants may have ODs just slightly less than diameter of the cannula lumen (which may be an inner diameter even if there are internal surface threads on the cannula lumen).

The implants herein may be cylinders of bone with a central lumen extending therethrough.

The implant herein may be allografts, may be ceramic, may be alloys, may comprise hydroxyapatite, may comprise calcium phosphate, and/or may comprise one or more polymeric materials.

In some examples the implants herein may be 15 mm to 35 mm in length (from proximal end to distal end), wherein implant 460 is an example of such a length range. In some examples the implants herein may have an outer diameter from 3.0 mm to 4.5 mm, optionally from 3.2 mm to 4.1 mm, wherein implant 460 is an example of such a diameter range.

A general method of implanting an SI joint stabilizing implant (such as implant 350 or 460) includes positioning a cannula (e.g., 310) removably coupled with a stylet (e.g., 320, or as shown in FIGS. 4 and 5) adjacent to an SI joint, the stylet disposed through a cannula lumen (e.g., 312) with a sharp distal end (e.g., 322) of the stylet, including a distal tip 326, extending 20 mm-40 mm (optionally 30 mm) distally from a cannula distal end (e.g., 316); advancing, in a dorsal approach, the sharp distal end of the stylet down and into the SI joint while the stylet is within the cannula lumen, wherein advancing the sharp distal end of the stylet into and down the SI joint disrupts the SI joint, preparing the SI joint to receive an SI joint implant; withdrawing the stylet from the cannula lumen while maintaining the cannula in position adjacent to the SI joint; positioning an SI joint implant into the cannula lumen; advancing the SI joint implant distally through the cannula lumen and down and into the SI joint with a plunger or tamp; withdrawing the plunger from the cannula, and removing the cannula from the subject while leaving the implant in the patient. An optional second implant may also be implanted adjacent and parallel to the first implant. As set forth above, the procedure herein utilize fewer components and require less time than procedures using other combinations of instruments, such as the system of instruments shown in FIG. 1.

In alternative methods, the cannula may be advanced to the level of the joint (and optionally docked at the joint) and the stylet may then be advanced into the proximal end of the cannula lumen, through the lumen, and advanced into the joint. Or in any of the methods herein, the cannula and stylet may be advanced together to the level of the joint but with the sharp distal end of the stylet not advanced beyond the distal end of the cannula (i.e., still within the cannula lumen), wherein the sharp distal end of the stylet may be advanced distally from the cannula after the combination of cannula and stylet is at or near the level of the joint.

Methods of preparation and implant delivery herein may specifically exclude the use of an obturator, an orientation guide, a decorticator, and one or more guide pins, examples of which are shown in FIG. 1. The methods herein, including claims, may thus be considered to inherently include the negative limitation of not including steps that require or use any of the components herein that are not needed.

A method of positioning any of the SI joint implants herein can include one or more planning steps to determine a desired entry point and/or trajectory. It is understood that figures herein that include planning (including trajectory planning) are exemplary and may not necessarily need to be performed (and not all steps included in any figure are necessarily performed). Additionally, the order of steps may vary to some extent and the implantation process may still be satisfactorily and safely completed.

Figure 8:
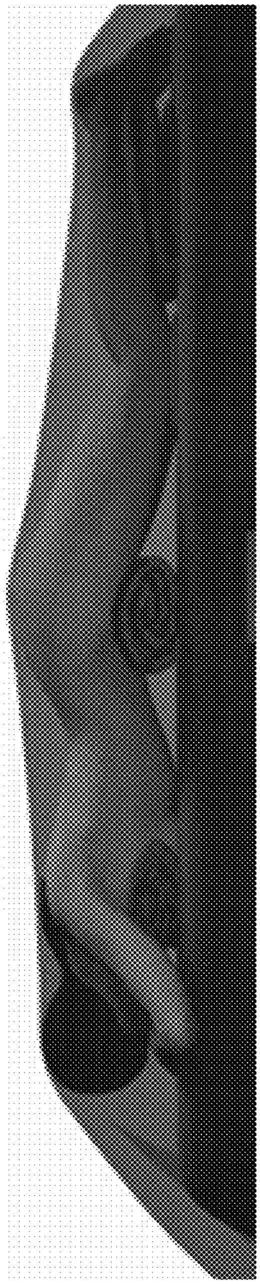
FIG. 8 illustrates an exemplary patient position for procedures herein.

FIG. 8 illustrates an exemplary patient set up and prone positioning for the procedures described herein.

Figure 9:
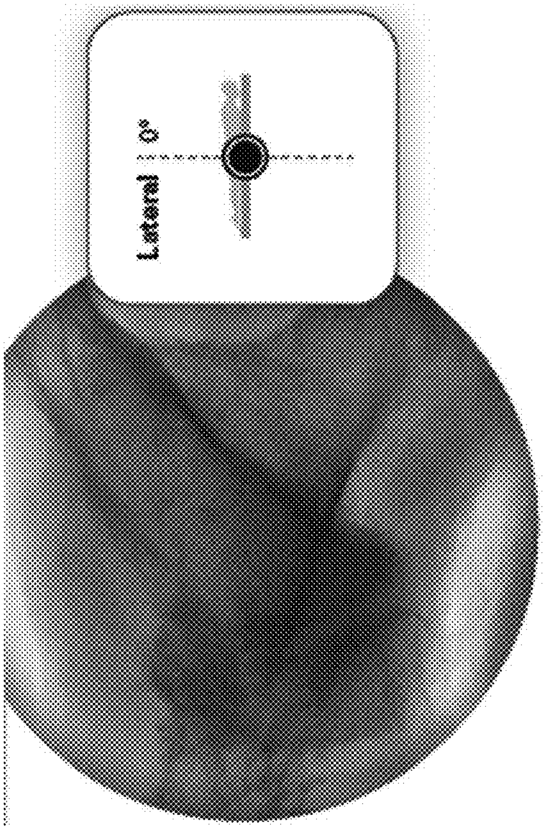

With reference to the exemplary lateral view of FIG. 9, the alar lines can be aligned by superimposing the left and right cortical densities. Next, the sciatic notches are aligned using C-arm swivel. The sciatic notches should remain superimposed throughout the procedure.

Figure 10:
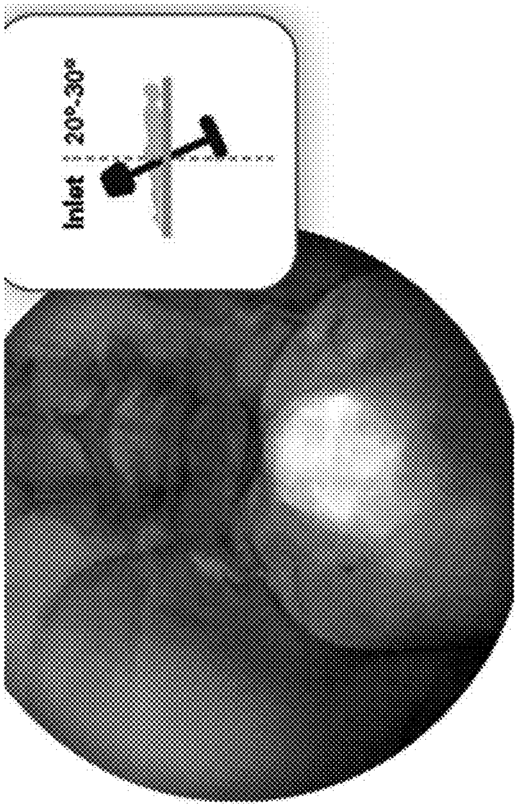
FIGS. 9, 10, 11, 12 and 13 illustrate exemplary planning for the SI joint implant implantation.

With reference to the inlet view of FIG. 10, the fluoroscope is tilted toward the feet until the dense cortical line of the S1-S2 vestigial disc directly overlines the dense cortical line of the sacral promontory. The beam in this view should line up with the anterior cortex of the S1 sacral body.

Figure 11:
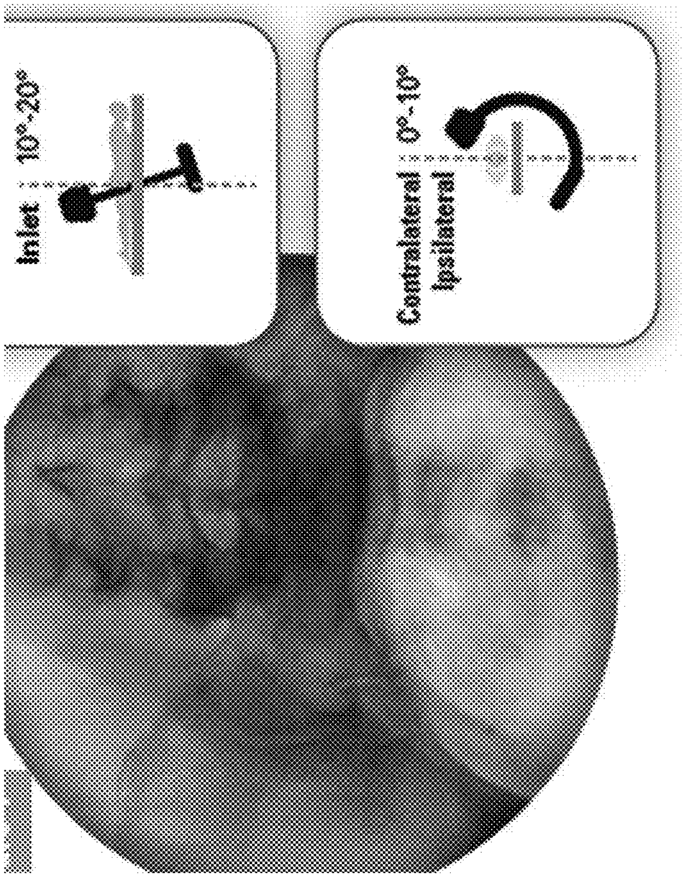

With reference to the INTRA view of FIG. 11 (which is −10 degrees cephalad from the inlet view and slightly oblique ipsilateral or contralateral), the beam in this view will optimize visualization of the posterior aspect of the inferior limb of the articular SI joint. The posterior aspect of the inferior limb of the articular SI joint is the medial joint in this view.

Figure 12:
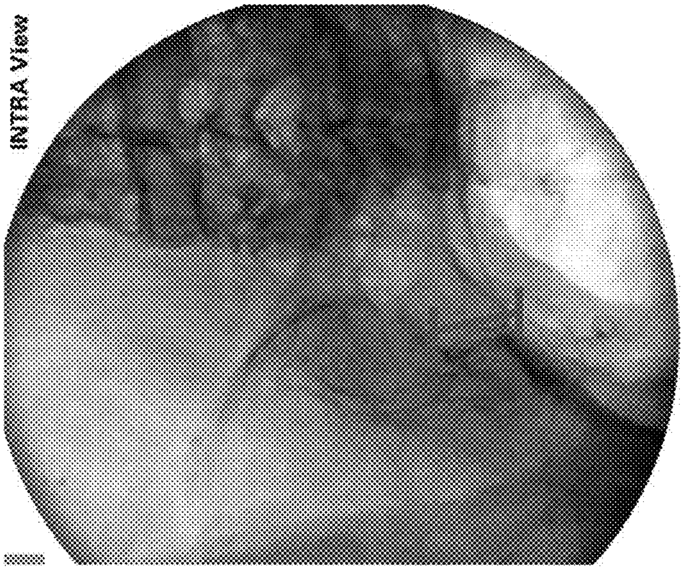
Figure 13:
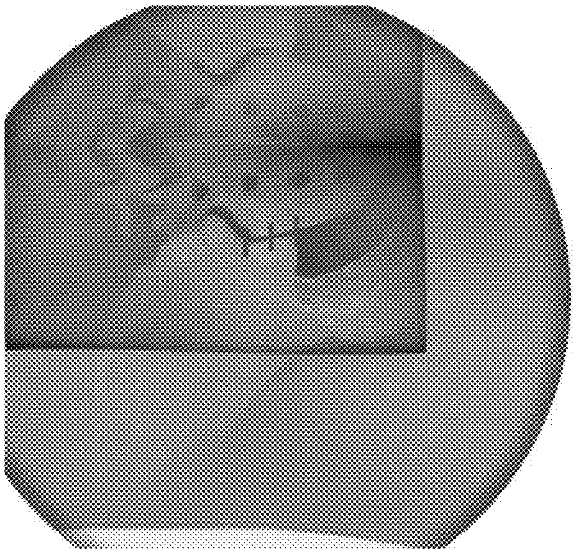

With reference to FIG. 12, in the INTRA view, method can include localizing the inferior aspect of the joint by placing an 8 gauge bone access needle on the skin. Mark on the skin where the medial joint meets the pelvic brim, and trace a 2 cm line posteriorly along the joint, as shown. As shown in FIG. 13, mark the center point, and make an incision at the center marking.

Figure 14A:
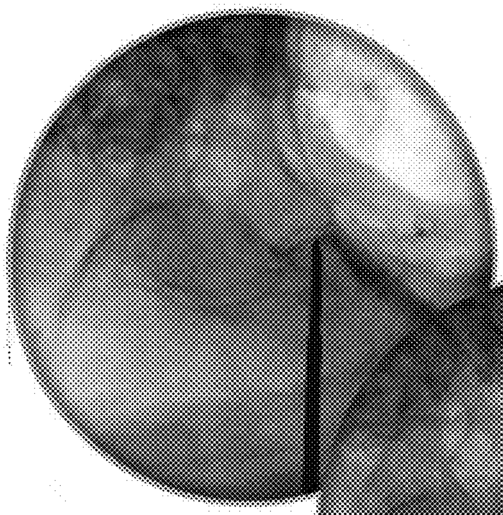
FIGS. 14A and 14B illustrate an exemplary trajectory for the stylet/cannula.
Figure 14B:
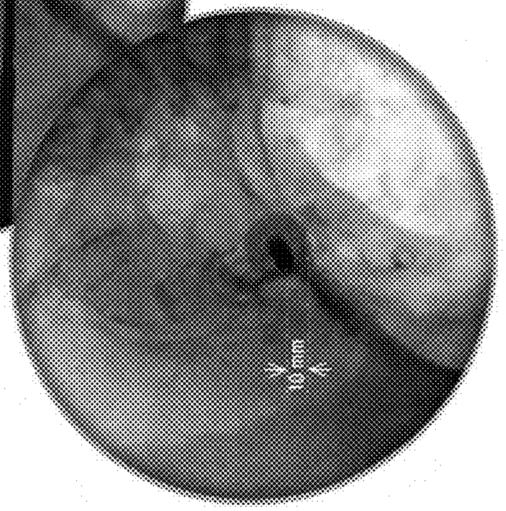

After making an incision, the procedure includes advancing the integrated stylet/cannula (e.g., as shown in FIGS. 4 and 5) to a target position with a target trajectory within the patient, which facilitates placement of the implant through the cannula, as is described below. First, the integrated stylet 412/cannula 410 is placed through the incision and preferably docked in the inferior third of the joint and approximately 10 mm from the anterior pelvic brim, as shown in FIGS. 14A and 14B. The integrated assembly is preferably angled such that it is aligned with the trajectory of the C-arm in the optimized INTRA view, with confirmation that the integrated system is visualized as a dot, as shown in FIG. 14B.

As shown in the trajectory of FIG. 15A (compared with FIG. 15B), the trajectory of the integrated system is adjusted to be parallel to the sciatic notch. The integrated system is advanced approximately 1 cm with tapping of a mallet.

Figure 16A:
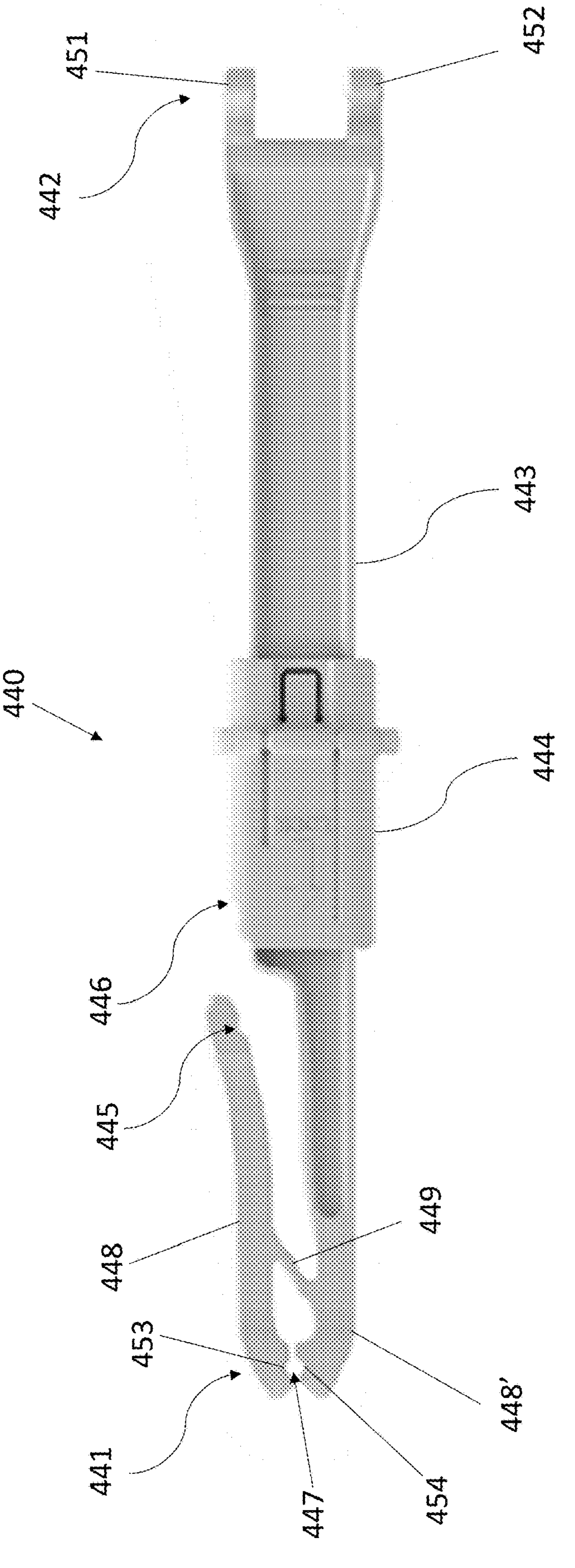
FIG. 16A illustrates an exemplary optional stabilization tool with a clamp end.
Figure 16B:
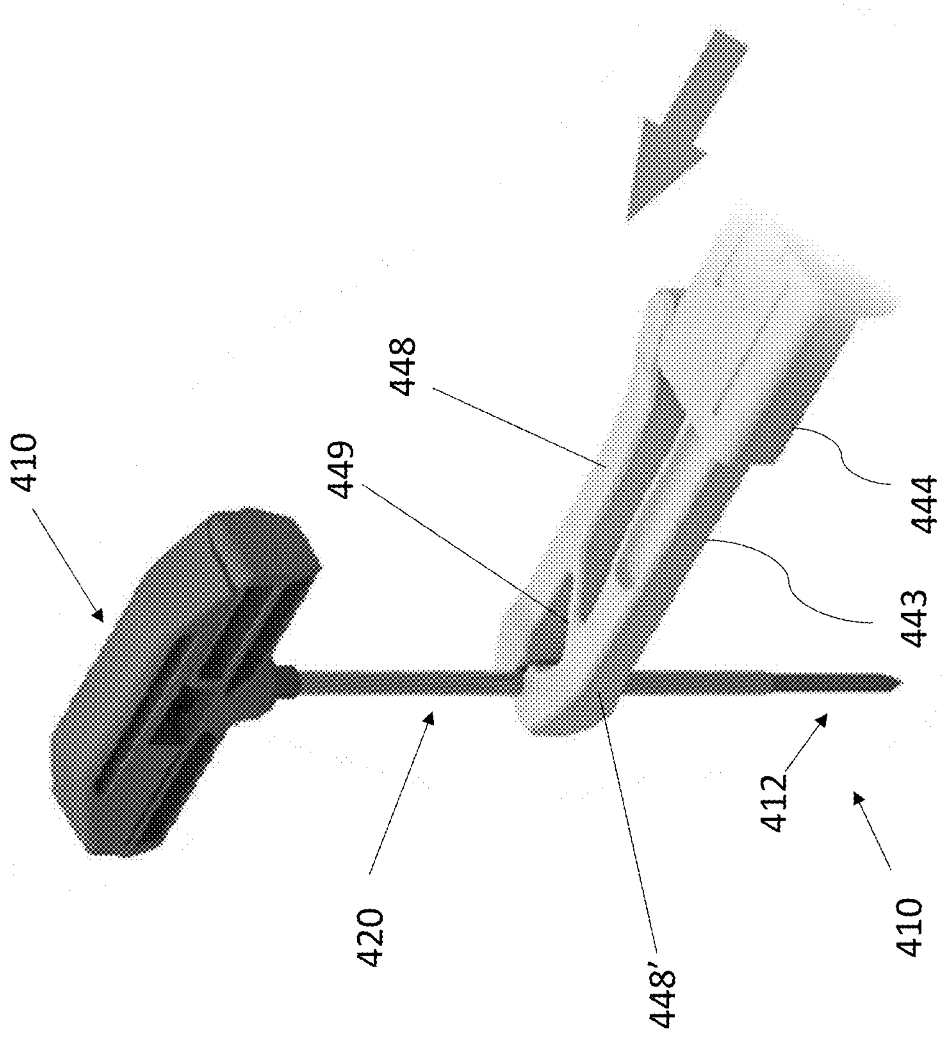
FIG. 16B illustrates the exemplary optional stabilization tool from FIG. 16A clamp around a cannula.

Optionally, tool 440, shown in FIGS. 16A and 16B, may be used to assist with holding and maintaining the positioning and trajectory of the integrated cannula/stylet, as shown in FIG. 16B. Tool 440 is, in this example, a combination function tool with a clamp end 441 and a lever end 442 with first and second hooks (although optionally tool 440 may only be configured as only one of a clamp or lever). The clamp end 441 is configured to clamp and hold the cannula to allow the user to indirectly hold the cannula while keeping their hand away from the radiation source. The movable collar 444 is adapted to be advanced relative to tool elongate body 443 to apply a force to the first end of arm or jaw 448, rotating the arm 448 about pivot 449 and causing the other clamp end of jaw 448 to apply an inward force and securely clamp a cannula within space 447 against the opposing jaw of tool 440. Lock element 445 on arm/jaw 448 is sized and configured to interface with lock element 446 on collar 444 to axially lock the collar in place, maintaining the clamping force around the cannula that is placed in cannula space 447, as shown in FIG. 16B (only a distal portion of tool 440 is shown in FIG. 16B; lever end not shown). The arrow in FIG. 16B represents advancing collar 444 forward to lock the collar in place and maintain a clamping force around cannula 420. Stylet 410, including distal portion 412 extending from cannula 420, is also shown in FIG. 14B. The lever end 442 of tool 440, described in more detail below, includes two hooks that are configured to be positioned in the cavities of the handle end of the stylet (after it's rotated 90 degrees relative to the cannula), and then by pressing down on the body 443 of tool 440, the stylet can be loosened from the bone and removed from the cannula. The combined stylet 410 and cannula 420, as well as tool 440, are described in further detail, with respect to the following exemplary steps of the procedure.

Tool 440 is an example of a tool comprising clamp end 441 comprising a first jaw 448 movable relative to a second jaw 448' about a pivot 449 (comprising an elongate body as shown), the first jaw 448 including a first locking element 445; a locking collar 444 axially movable relative to the elongate body 443, the locking collar including a second locking element 446 sized and configured to interface with the first locking element 445 to maintain the collar 444 in a locked position relative to the elongate body 443 and prevent clamp ends of the first and second jaws from moving away from one another. Tool 440 also includes a lever end 442 opposite the clamp end 441 along the length of elongate body 443, the lever end 442 comprising first and second hooks 451, 452. Each of hooks 451 and 452 has a curved configuration including a recessed surface as shown, the curved first and second hooks extending from the elongate body, and each of the first and second hooks sized and configured to accommodate and interface with a proximal handle portion of a stylet to facilitate application of a removal force to the proximal handle portion of the stylet, as shown in in FIGS. 19B, 19C, 20A and 20B. As shown in FIG. 16A, each of first and second jaws 448 and 448' has a recessed surface, 453 and 454 respectively, facing one another (inward) and together defining a cannula space 447, the recessed surfaces 453, 454 each concave (as shown) to interface with an outer surface of a cannula and clamp the cannula in space 447. As shown, pivot 449 comprises an elongate body extending between first jaw 448 and second jaw 448' at a location proximal to the clamp ends of each of the first and second jaws.

Figures 17A, 17B:
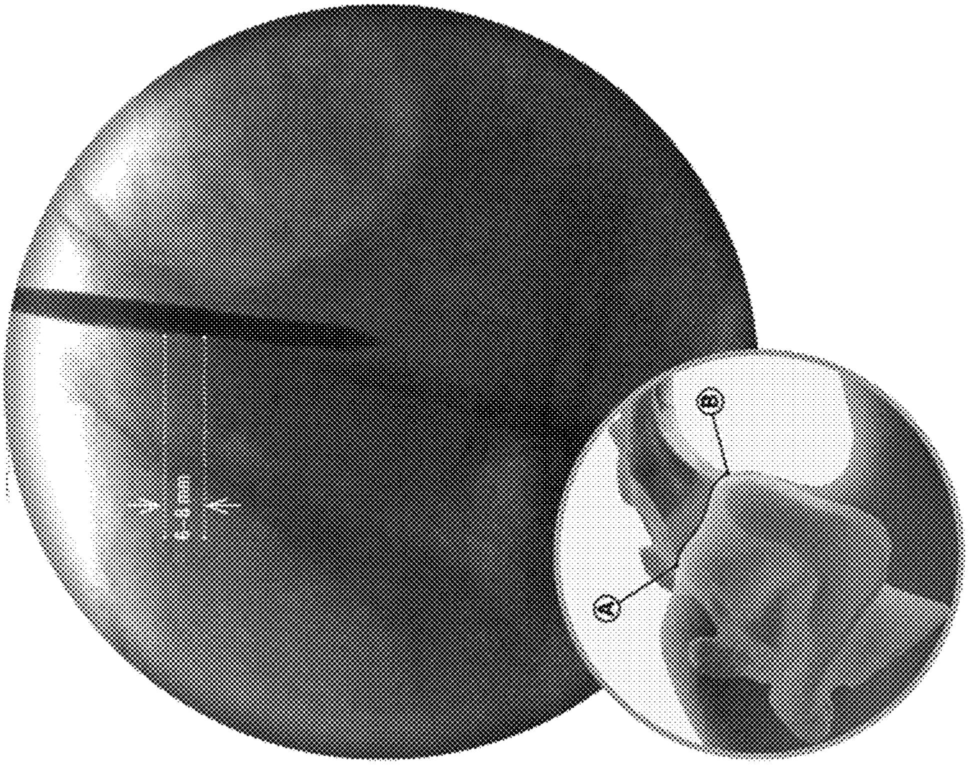
FIGS. 17A and 17B illustrate views related to confirming a trajectory of the stylet.

With reference to FIGS. 17A and 17B, the trajectory of the stylet can be confirmed with the lateral view. This may include identifying where the iliac crest intersects the dorsal aspect of the sacrum (location "A" in FIG. 17B); identifying where the sciatic notch intersects the ventral aspect of the sacrum (location "B" in FIG. 17B); the line connecting these two points (as shown in FIG. 17B) is the posterior aspect of the inferior limb of the joint and can be used to determine depth; and advancing the integrated stylet/cannula until the cannula is 6-8 mm below the posterior aspect of the joint. Placing the stylet too deep may result in difficulties removing the stylet from the cannula.

Figure 18:
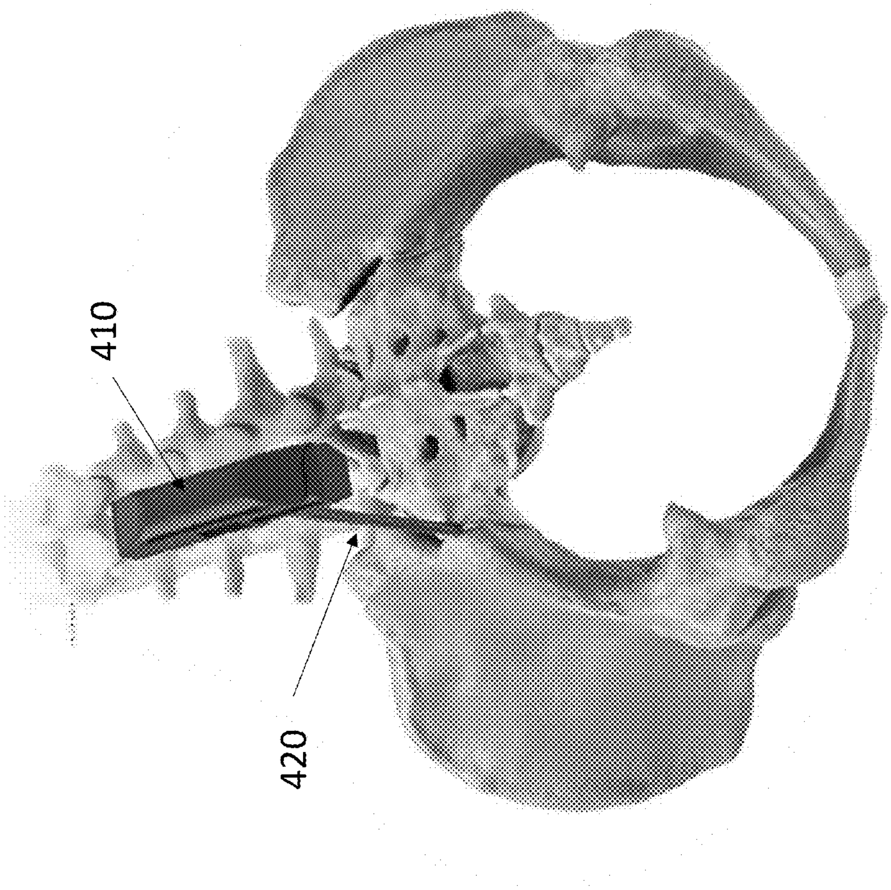
FIG. 18 represents a position and trajectory of an integrated cannula/stylet with a distal region of the stylet/cannula within the inferior limb of the SI joint.

FIG. 18 represents the position and trajectory of the integrated cannula 420/stylet 410 with a distal region of the stylet/cannula within the inferior limb of the SI joint and with the cannula 6-8 mm below the posterior aspect of the joint.

Figures 19A, 19B, 19C:
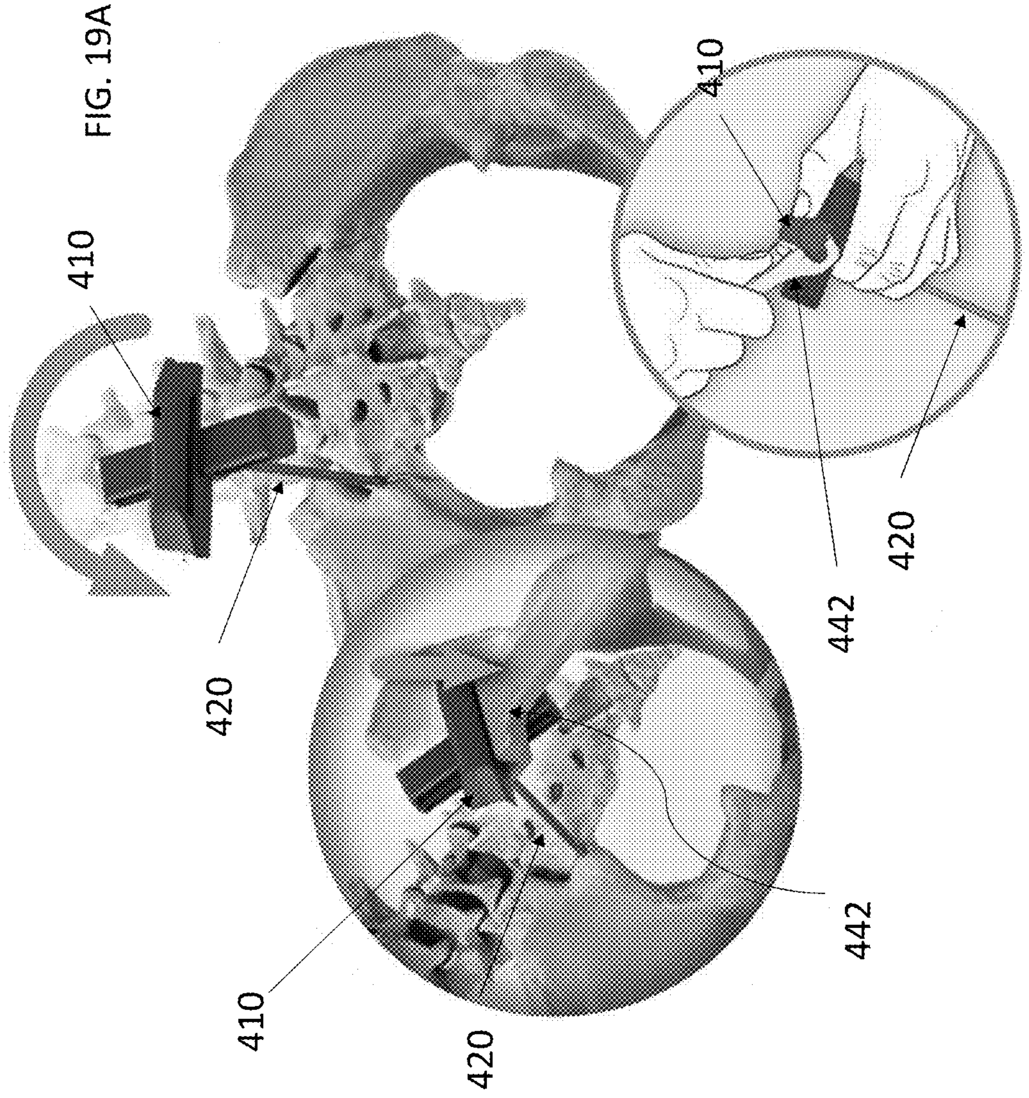
FIGS. 19A, 19B and 19C illustrate a stylet loosening/removal process.
Figure 20B:
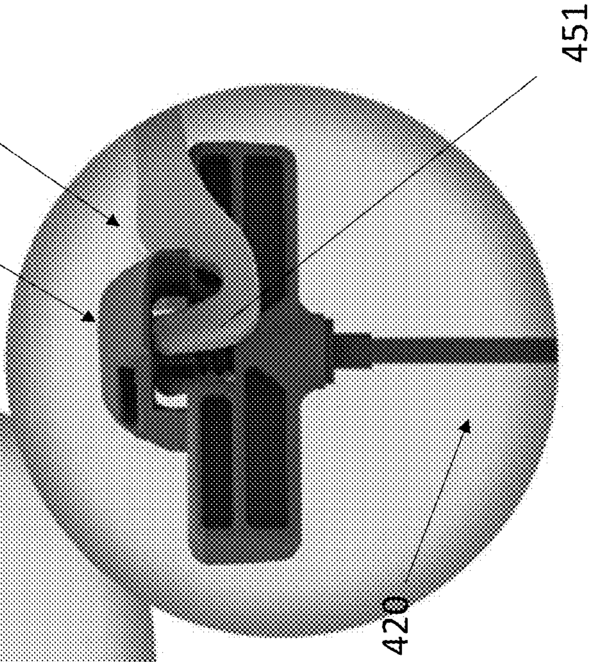
FIGS. 20A and 20B illustrate using a lever end of a tool to remove a stylet.
Figure 20A:
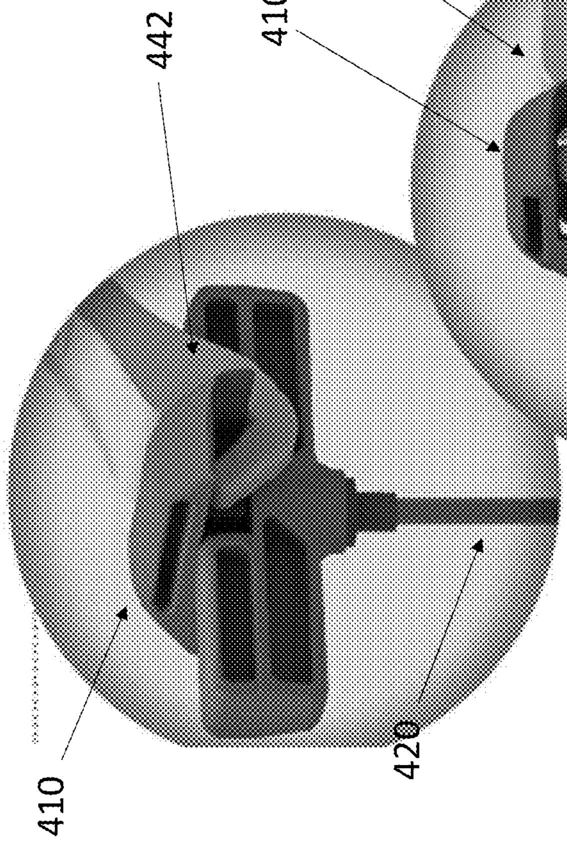

Once the cannula is advanced to the desired depth, and the stylet has prepped the joint, the stylet is removed from the cannula. FIGS. 19A, 19B and 19C illustrate an exemplary stylet loosening and/or removal process, optionally using lever portion 442 of tool 440. The stylet 410 is first turned 90 degrees relative to the cannula 420, as shown by the arrow in FIG. 19A. The hooks of lever portion 442 of tool 440 are then positioned in the cavities of the handle end of the stylet, as shown in FIG. 19B. While holding the cannula with one hand, the other hand applies downward force on tool 440 to loosen the stylet from the bone and remove the stylet from the cannula, as shown in FIG. 19C. FIGS. 20A and 20B provide additional closeup views of the hooks of lever end 442 of tool 440 being inserted into the proximal handle portion of stylet, followed by pressing down on tool 440 to loosen stylet 410 and raise it relative to cannula 420.

Figure 23:
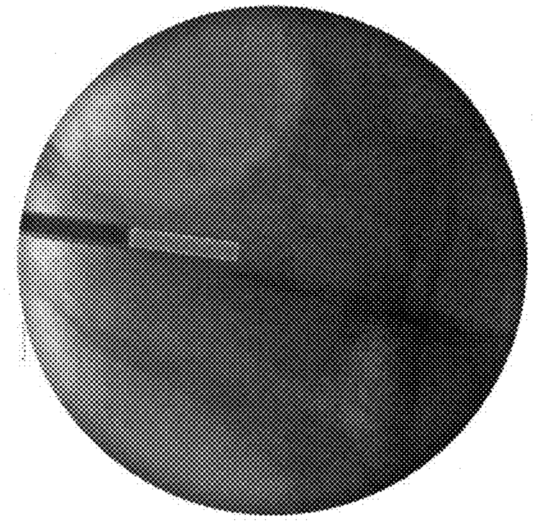
FIG. 23 illustrates an exemplary preferred position of an SI joint implant.

After the stylet has been removed, implant 460 (or other implant herein) is placed into the cannula lumen proximal end, as shown in FIGS. 21 and 22. Tamp or plunger 460 is placed into the cannula lumen and used to push implant 460 through cannula 420 to depth. The position of the cannula 420 should be maintained while advancing the implant to prevent the cannula from being further distally advanced (optionally by holding the cannula with the clamping end of tool 440). The implant may continue to be advanced by gently hitting the proximal end of the tamp 460 with mallet 450 to the positive stop, as shown in FIG. 22. With reference to FIG. 23, the proximal end of the implant should be 6-8 mm below the posterior aspect of the SI joint, which is well short of the iliac cortical densities (ala line).

Figure 24B:
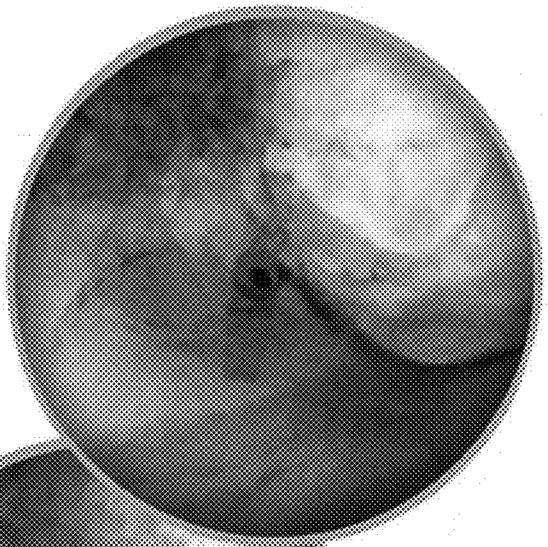
FIGS. 24A and 24B illustrate an exemplary trajectory for a second implant.
Figure 24A:
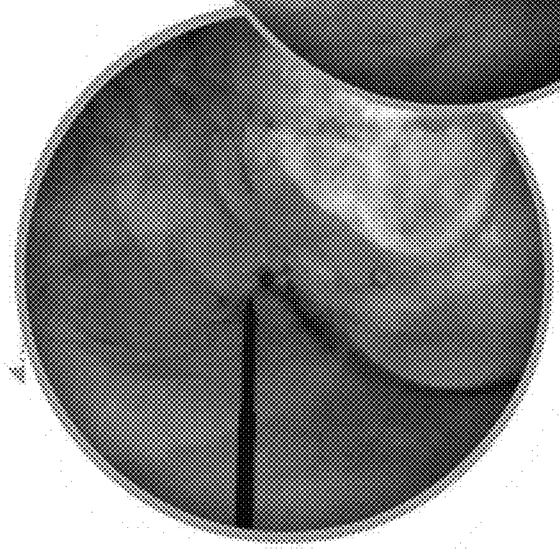
Figure 25:
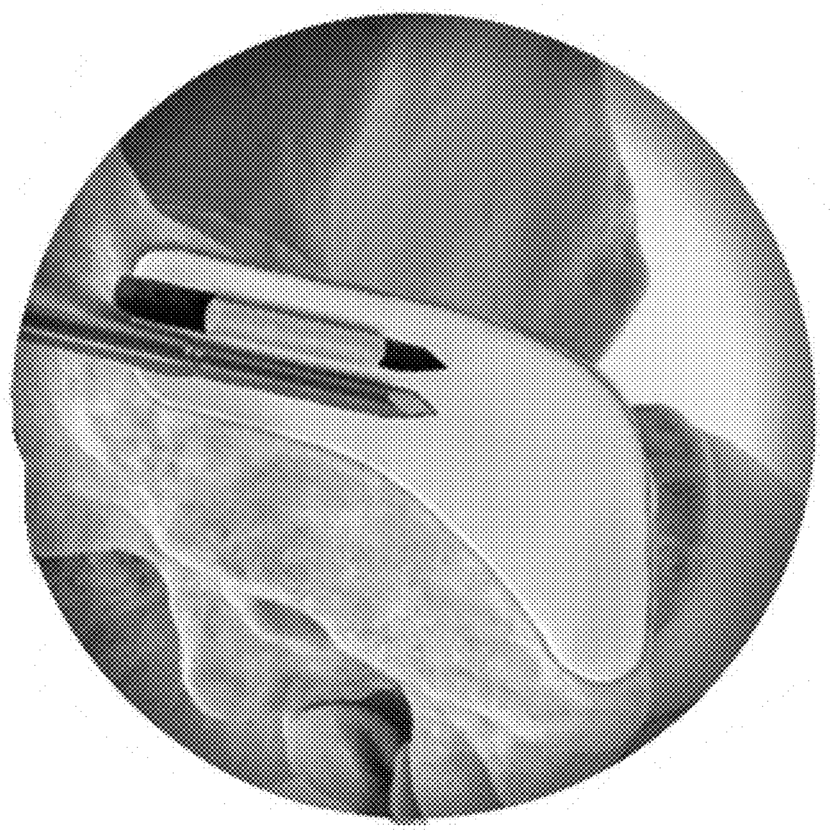
FIG. 25 illustrates stylet advanced parallel to a first implant.

Optionally, any of the procedures herein may include implanting a second implant with a similar procedure to that of the first implant, and parallel to the first implant, which is described with reference to FIGS. 24A, 24B, 25, 26A, 26B, and 26C. With reference to FIGS. 24A and 24B, a second implant should be placed at the junction of the middle third and dorsal third of the SI joint and parallel to the first implant. The stylet is first reinserted into the cannula lumen. In the INTRA view, the integrated stylet/cannula is repositioned to access the junction of the middle third and dorsal third of the SI joint. This is preferably minimum 5 mm of distance center-to-center between the first and second implants. Confirming the cannula/stylet is a dot in the INTRA view when placing the second implant ensures the implants are parallel. The process for implanting the first implant as set forth herein is then repeated for the second implant. FIG. 25 illustrates the stylet/cannula after being advanced adjacent and parallel to the first implant.

Figure 26A:
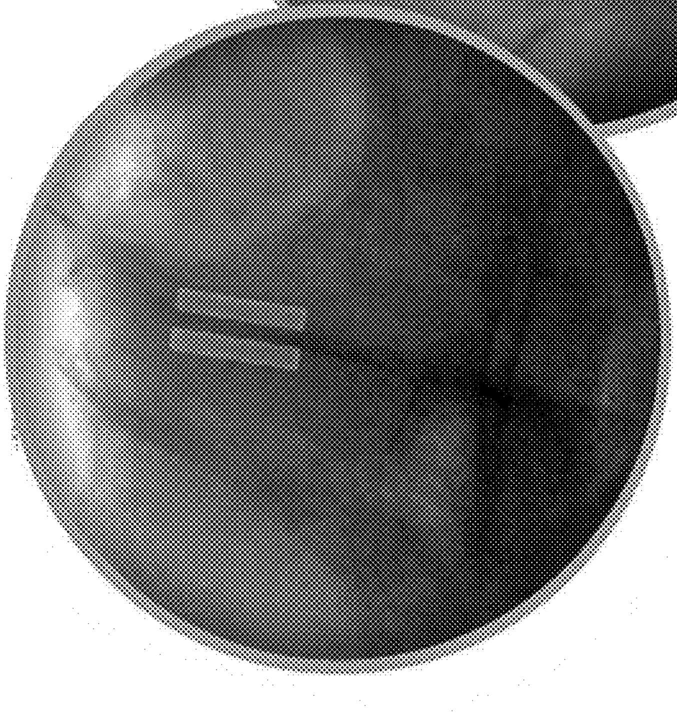
FIGS. 26A, 26B and 26C illustrate first and second implants positioned in an SI joint.
Figure 26B:
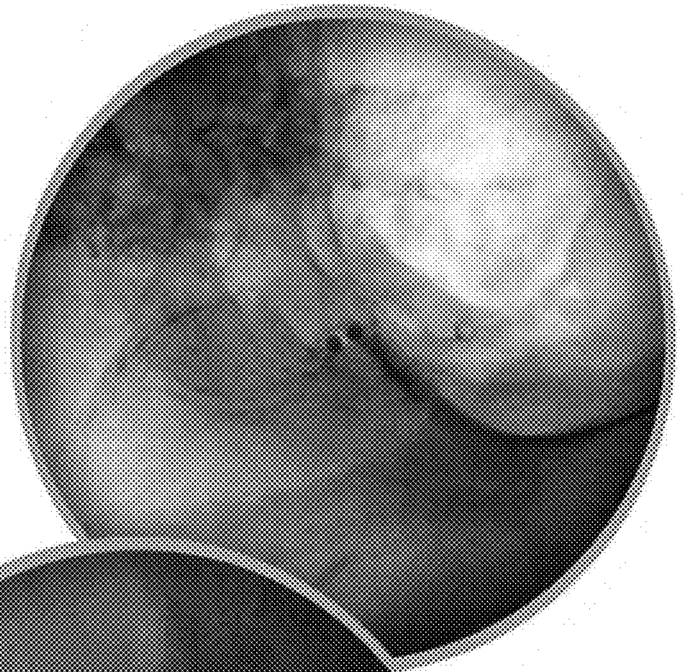
Figure 26C:
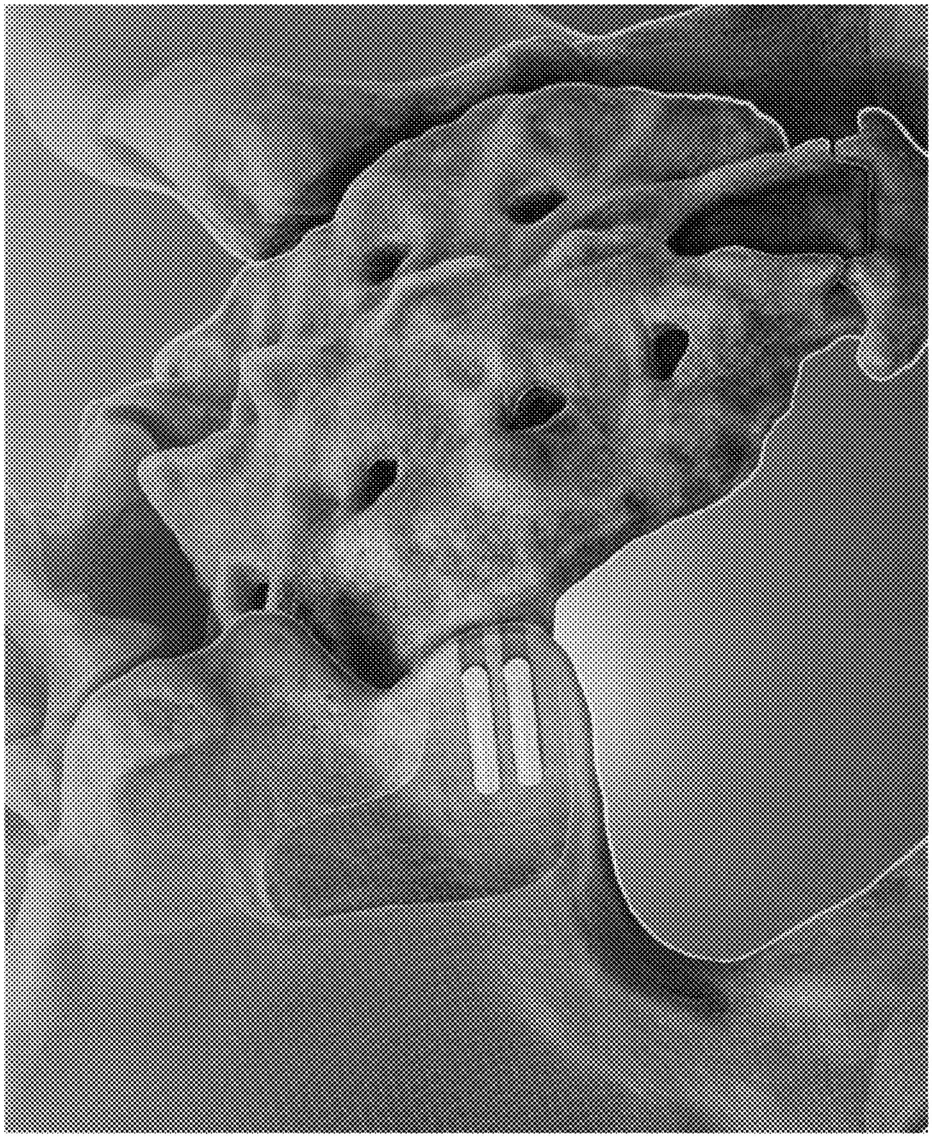

FIGS. 26A and 26B illustrate two views of two implants implanted down the SI joint and parallel (or nearly parallel) to each other as described herein. FIG. 26C is a representation of the final implant location of two implant down the SI joint as described herein, with the preferred trajectory and placement shown in FIG. 15A.

The invention claimed is:

1. A method of positioning a sacroiliac (SI) joint implant, comprising:

in a dorsal trajectory, positioning a stylet removably coupled with a cannula adjacent to an SI joint, the stylet disposed through a cannula lumen with a sharp distal end of the stylet 20 mm-40 mm extending distally from a cannula distal end;

advancing, in the dorsal trajectory, the sharp distal end of the stylet into the SI joint, while a portion of the stylet is within the cannula lumen, to disrupt the SI joint and prepare the SI joint to receive an SI joint implant;

removing the stylet from the SI joint and from the cannula lumen, leaving the cannula distal end adjacent to the SI joint;

positioning an SI joint implant into the cannula lumen;

advancing the SI joint implant with a plunger distally through the cannula lumen and into the SI joint; and removing the cannula from a subject while leaving the implant in the SI joint.

2. The method of claim 1, wherein the sharp distal end of the stylet is 25 mm-35 mm distally from the cannula distal end.

3. The method of claim 1, wherein advancing the stylet and cannula comprises advancing the stylet and cannula in a trajectory in line with a ventral cortex of a inferior limb of an articular surface of the SI joint.

4. The method of claim 1, wherein advancing the stylet comprises advancing the stylet until the sharp distal end of the stylet is caudal and ventral to an iliac cortical density/alar line.

5. The method of claim 1, wherein the method does not include the use of an obturator, a decorticator, and an orientation guide.

6. The method of claim 1, wherein advancing the SI joint implant distally comprises applying an axially directed force on the SI joint implant with the plunger.

7. The method of claim 1, wherein removing the stylet from the SI joint and from the cannula lumen comprises rotating the stylet relative to the cannula, and using a lever end of a tool to loosen the stylet from bone.

8. The method of claim 1, further comprising clamping an outer surface of the cannula with a clamp end of a stabilizing instrument to stabilize the cannula.

9. The method of claim 1, wherein the SI joint implant is a first implant, the method further comprising implanting a second implant in the dorsal trajectory, in the SI joint, and parallel to the first implant.

10. The method of claim 9, wherein the first and second implants are implanted in an inferior limb of the SI joint through an articular portion of the SI joint.

11. A method of positioning a sacroiliac (SI) joint implant, comprising advancing, in a dorsal approach, a cannula to a level of an SI joint;

advancing a sharp distal end of a stylet into or adjacent to the SI joint while a portion of the stylet is within a cannula lumen, wherein the sharp distal end of the stylet is positioned 20 mm-40 mm distally from a cannula distal end, and wherein advancing the sharp distal end of the stylet into or adjacent to the SI joint disrupts the SI joint and prepares the SI joint to receive an SI joint implant;

removing the stylet from the cannula lumen and leaving the cannula adjacent to the SI joint;

positioning an SI joint implant into the cannula lumen;

advancing the SI joint implant distally through the cannula lumen and into the SI joint; and removing the cannula from a subject while leaving the implant in the SI joint.

* * * * *